US008569578B1

(12) United States Patent
Wang et al.

(10) Patent No.: US 8,569,578 B1
(45) Date of Patent: Oct. 29, 2013

(54) **GENERATING TRANSGENIC POTATOES WITH NOVEL RESISTANCE TO POTATO CYST NEMATODES BY SILENCING NEMATODE PARASITISM GENES OF *CLE -1* AND *CLE-4S***

(75) Inventors: Xiaohong Wang, Ithaca, NY (US); Shunwen Lu, Fargo, ND (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 126 days.

(21) Appl. No.: 12/847,053

(22) Filed: Jul. 30, 2010

Related U.S. Application Data

(60) Provisional application No. 61/273,222, filed on Jul. 31, 2009.

(51) Int. Cl.

| | |
|---|---|
| ***C12N 15/113*** | (2010.01) |
| ***C12N 15/82*** | (2006.01) |
| ***C12N 5/10*** | (2006.01) |
| ***A01H 5/00*** | (2006.01) |

(52) U.S. Cl.
USPC ........ 800/279; 800/285; 536/24.5; 435/320.1

(58) Field of Classification Search
None
See application file for complete search history.

(56) References Cited

PUBLICATIONS

Mitchum et al. (2008) Curr. Opin. Plant Biol. 11: 75-81.*
Huang et al. (2006) PNAS 103: 14302-14306.*

* cited by examiner

*Primary Examiner* — David T Fox
*Assistant Examiner* — Steven Bernacki
(74) *Attorney, Agent, or Firm* — John D. Fado; Evelyn M. Rabin

(57) ABSTRACT

Plant CLAVATA3/ESR-related (CLE) peptides have diverse roles in plant growth and development. We have isolated and characterized the function of five new CLE genes from the potato cyst nematode *Globodera rostochiensis*. Unlike typical plant CLEs that contain a single CLE motif, four of the five Gr-CLE genes encode CLE proteins with multiple CLE motifs. These Gr-CLEs were found to be specifically expressed within the dorsal esophageal gland cell of nematode parasitic stages, suggesting a role for their encoded proteins in plant parasitism. Overexpression of Gr-CLEs in *Arabidopsis* mimicked overexpression of plant CLEs and Gr-CLE proteins could rescue the *Arabidopsis* clv3-2 mutant phenotype when expressed within meristems. A short root phenotype was observed when synthetic GrCLE peptides were exogenously applied to roots of *Arabidopsis* or potato similar to the overexpression of Gr-CLEs in *Arabidopsis* and potato hairy roots. These results reveal that *G. rostochiensis* CLEs with either single or multiple CLE motifs function similarly to plant CLEs and that CLE signaling components are conserved in both *Arabidopsis* and potato roots. Transgenic potato hairy roots expressing Gr-CLE-1 or Gr-CLE-4 dsRNA were generated. There was an approximately 50% reduction in the average number of cysts per root in the Gr-CLE-1 or Gr-CLE-4 dsRNA transgenic lines when compared with the infected control lines, indicating that silencing nematode CLE genes through host-derived RNAi may generate novel resistance against potato cyst nematodes in transgenic potatoes.

7 Claims, 13 Drawing Sheets
(4 of 13 Drawing Sheet(s) Filed in Color)

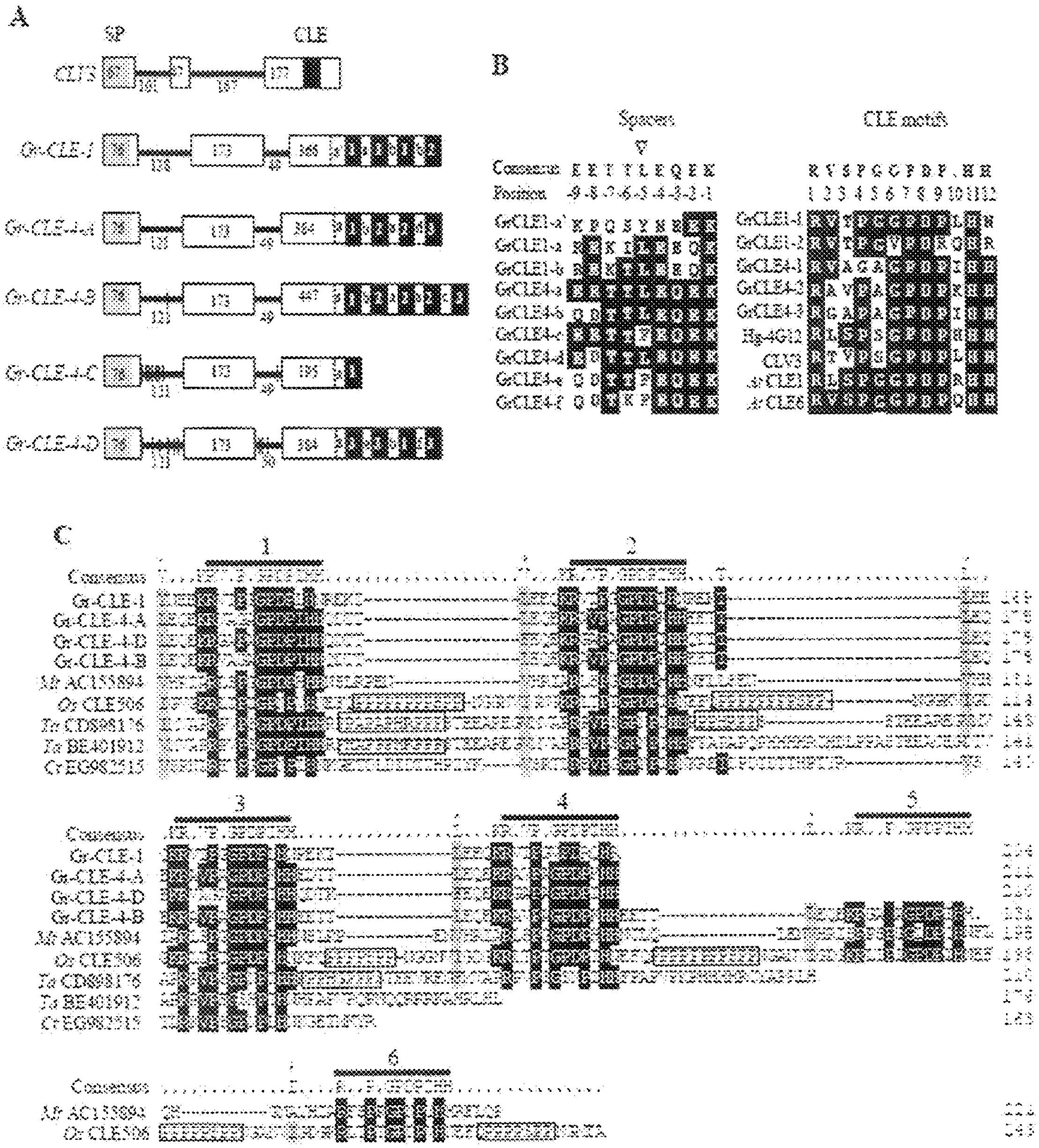
Fig. 1A-C

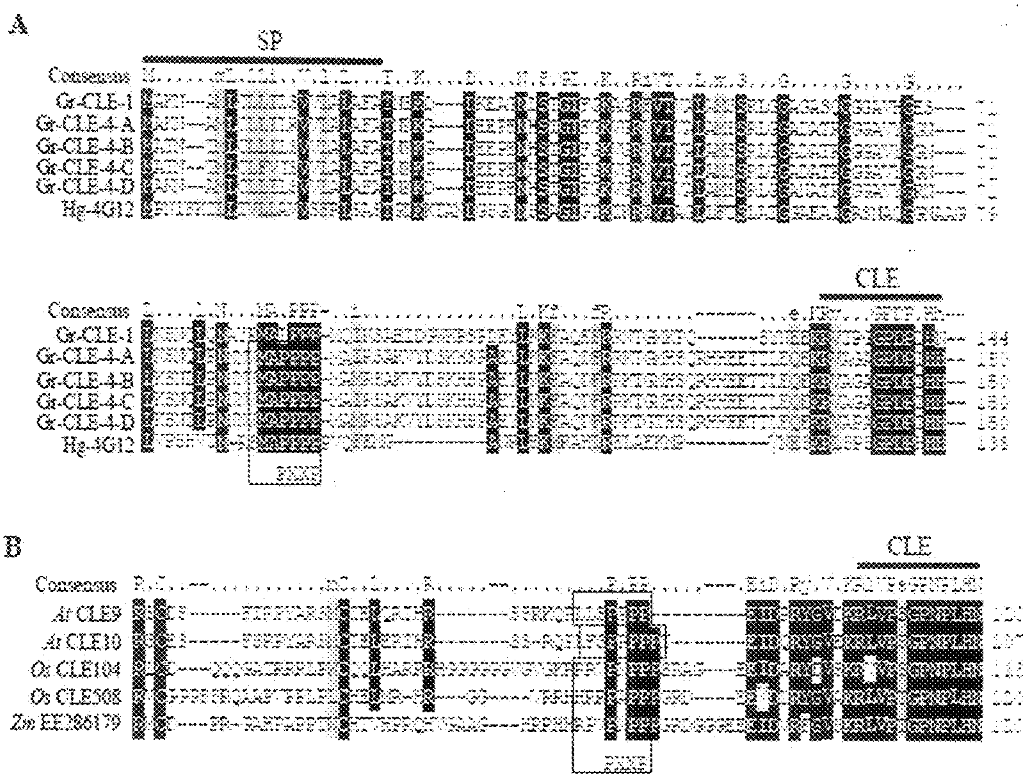
Fig. 2A-B

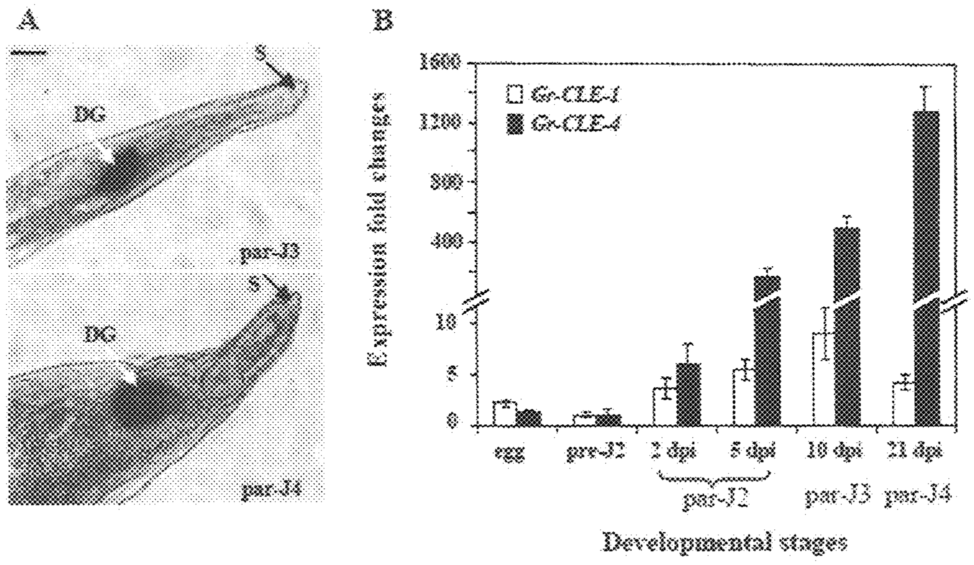
Fig. 3A-B

A
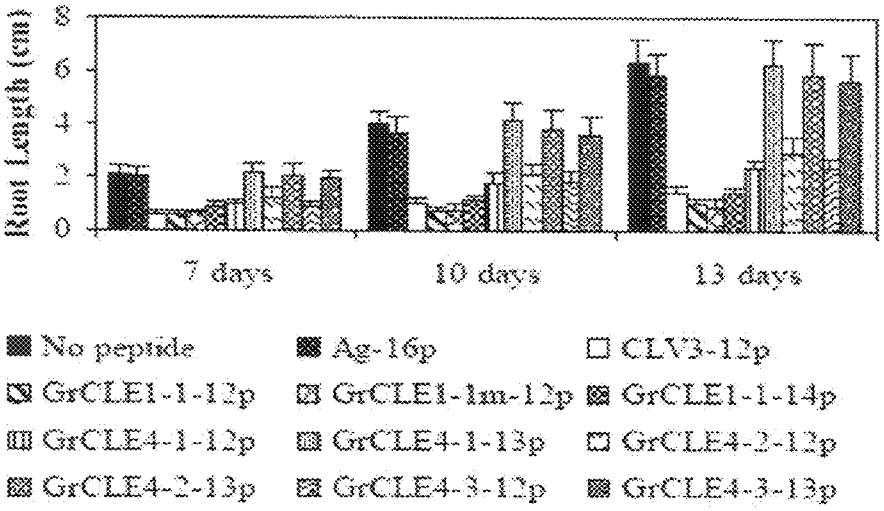
B
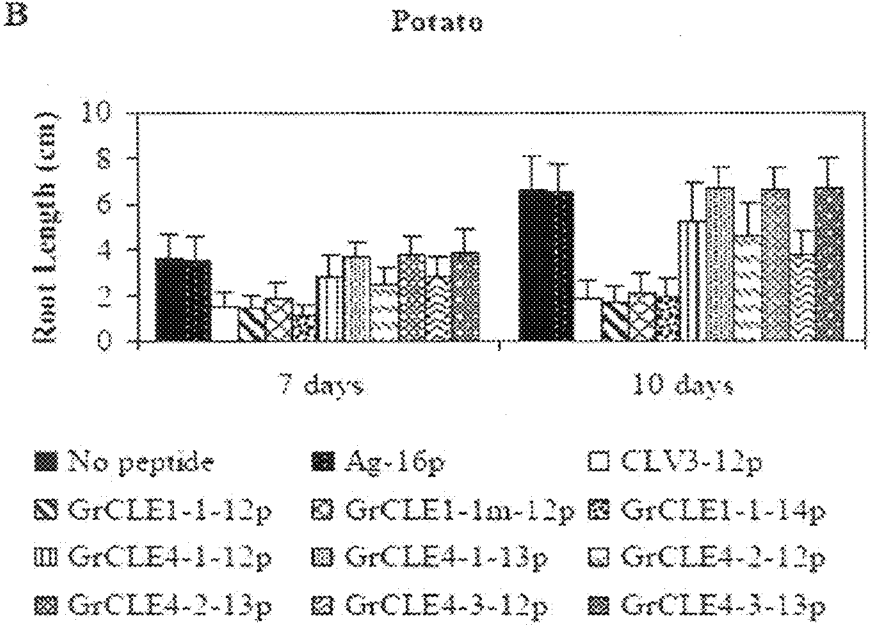
Fig. 4A-B

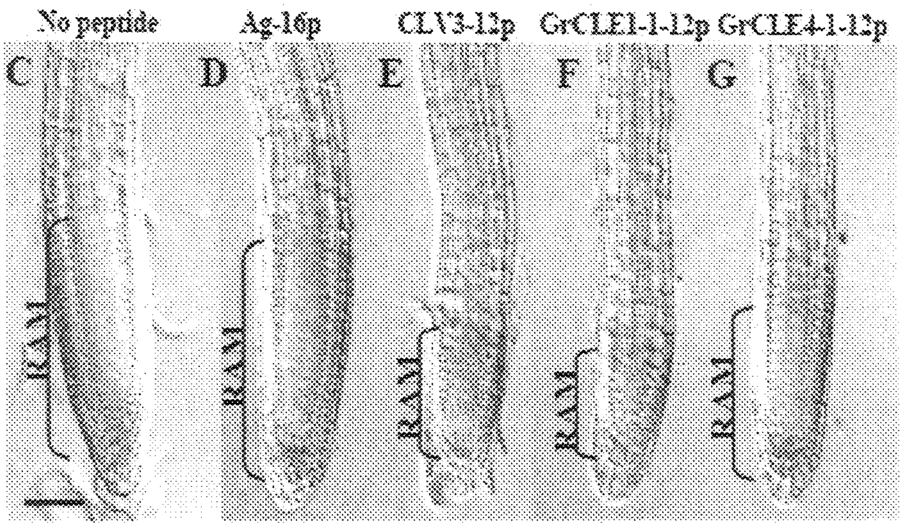
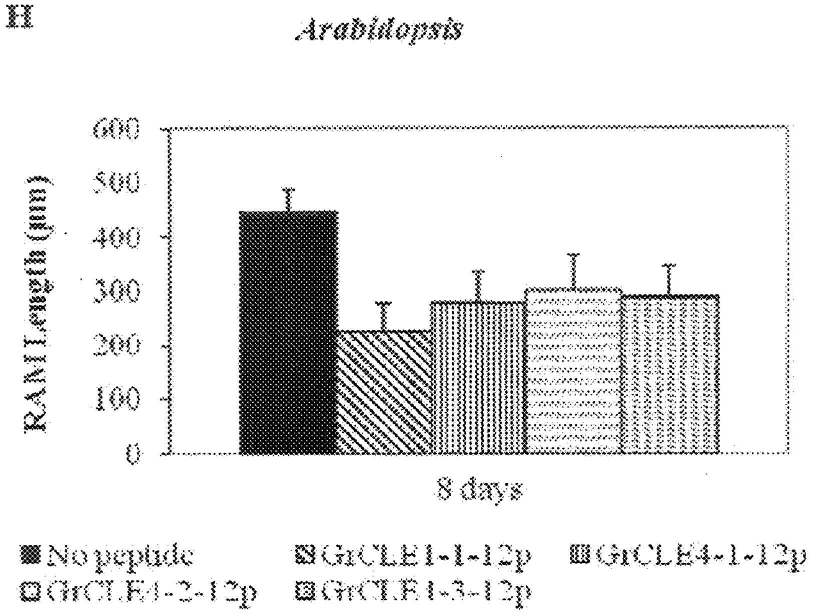
Fig. 4C-H

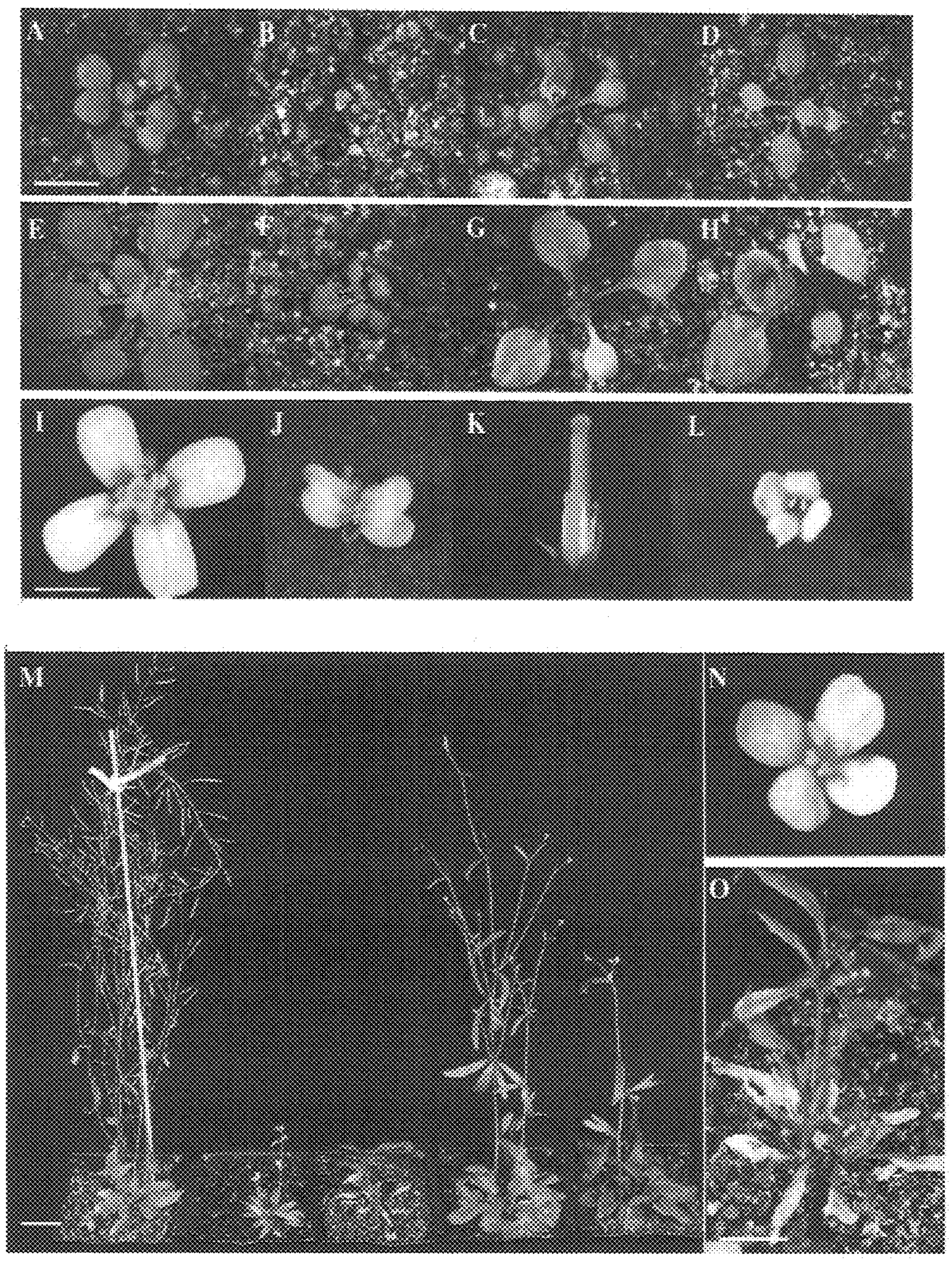
Fig. 6A-O

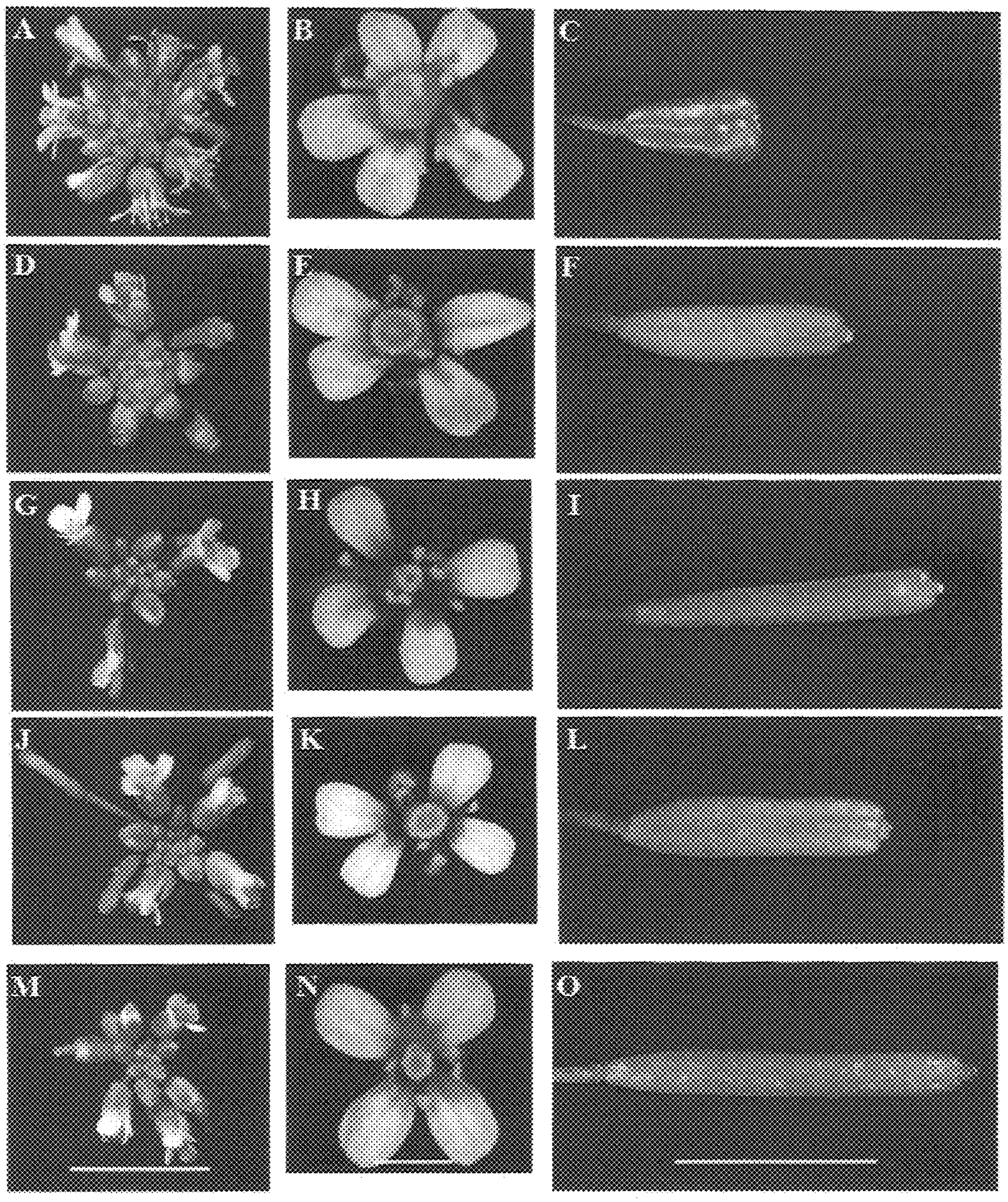
Fig. 7A-O

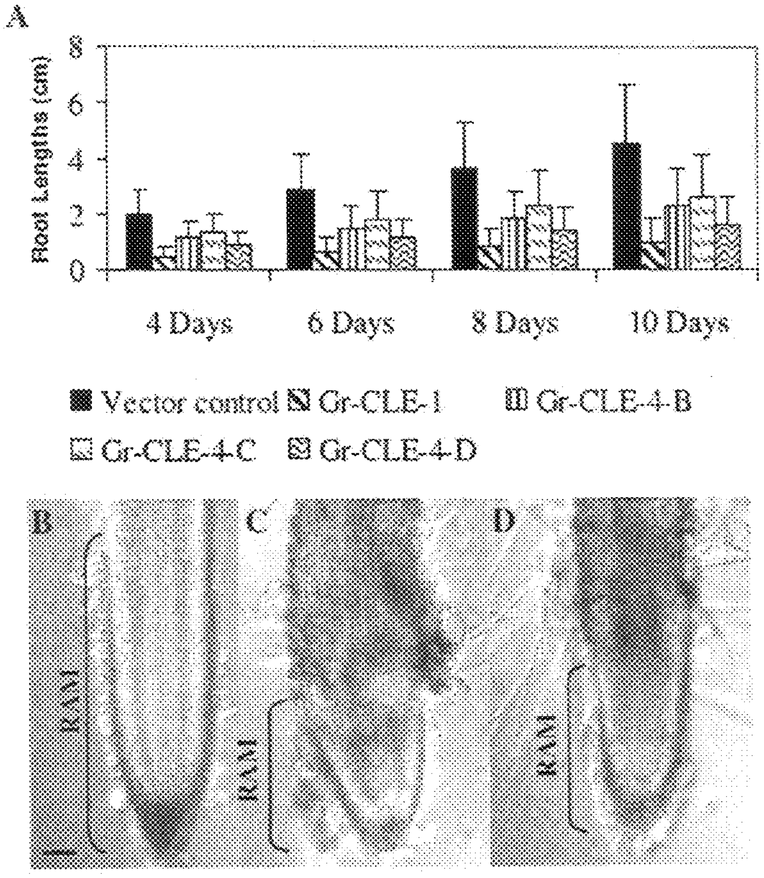
Fig. 8A-D

Fig. 10
Super promoter
Intron
PAnos
LB
RB

GENERATING TRANSGENIC POTATOES WITH NOVEL RESISTANCE TO POTATO CYST NEMATODES BY SILENCING NEMATODE PARASITISM GENES OF *CLE -1* AND *CLE-4S*

This application claims the benefit of U.S. Provisional Application No. 61/273,222, filed Jul. 31, 2009, which is incorporated herein by reference in its entirety.

BACKGROUND OF THE INVENTION

1. Field of the Invention

This invention relates to novel CLAVATA3/ESR (CLE) genes, GrCLEs, cloned from the potato cyst nematode *Globodera rostochiensis*, specifically expressed in the dorsal esophageal gland cell of nematode parasitic stages, Gr-CLE proteins with multiple CLE motifs, and a method of using host-derived RNA interference (RNAi) of Gr-CLE genes to generate novel resistance against *G. rostochiensis* in transgenic potatoes.

2. Description of the Relevant Art

Potato cyst nematodes (*G. rostochiensis* and *G. paffida*) are obligate root parasites that have evolved highly sophisticated parasitic relationships with specific host plants (Davis et. al. 2004. *Trends Parasitol.* 20:134-141; Hussey and Grundler. 1998. In: *Physiology and Biochemistry of Free-Living and Plant-Parasitic Nematodes*. R. N. Perry and D. J. Wright, eds. CAB International Press, Oxford, Pages 213-243). Infective second-stage juveniles (J2) hatch from eggs within the cyst in the soil and infect host roots. The J2 uses its stylet (hollow mouth spear) to aid its intracellular root migration and selects an initial cell within root tissues for the development of complex feeding structure called a syncytium (Dropkin, V. H. 1969. *Annu. Rev. Phytopathol.* 7:101-122.; Jones, M. G. K. 1981. *Ann. Appl. Biol.* 97:353-372). Juveniles of *G. rostochiensis* preferentially select a fully differentiated cortical cell in potato roots to initiate a syncytium (Jones and Northcote. 1972. *J. Cell Sci.* 10:789-809). At the onset of feeding, the nematode becomes sedentary and relies on the syncytium for nourishment for the remainder of its life cycle.

The formation of the syncytium represents one of the most complicated plant responses triggered by plant pathogens. The syncytium is a highly metabolically active multinucleate structure formed by extensive cell wall dissolution of neighboring cells around the initial syncytial cell. Its characteristics include enlarged nuclei and nucleoli, dense cytoplasm, increased numbers of subcellular organelles, small vacuoles, and thickened cell walls with elaborate wall ingrowths formed adjacent to the vascular tissues (Jones 1981, *Ann. Appl. Biol.* 97:353-372supra). The formation of wall ingrowths facilitates nutrient uptake from the xylem into the syncytium to meet the demands of the feeding nematode. Some of these developmental characteristics are features of various types of plant cells, inducing meristematic cells and transfer cells, suggesting that cyst nematodes have likely evolved mechanisms to manipulate plant developmental pathways to form a novel cell type (Mitchum et al. 2008. *Curr. Opin. Plant Biol.* 11:75-81).

Secreted proteins encoded by parasitism genes expressed within the single dorsal and two subventral esophageal gland cells of cyst nematodes represent the major functional molecules that directly or indirectly modulate plant cellular processes involved in the induction, formation, and maintenance of the syncytium (Davis et al. 2004, supra; Davis et al. 2008. *Curr. Opin. Plant Biol.* 11:360-366; Hussey, R. S. 1989. *Annu. Rev. Phytopathol.* 27:123-141.). Parasitism genes from the soybean cyst nematode (Heterodera glycines) encoding small secreted proteins with similarity to CLAVATA3/ESR-related (CLE) signaling peptides were identified previously (Gao et al. 2003. *Mol. Plant-Microbe Interact.* 16:720-726.; Olsen and Skriver. 2003. *Trends Plant Sci.* 8:55-57; Wang et al. 2001. *Mol. Plant Microbe Interact.* 14:536-544). This is the only known report of CLE genes outside the plant kingdom. Plant CLEs encode small proteins with an N-terminal signal peptide, a variable domain, and a conserved 14-amino acid (aa) domain called the CLE motif located at or near their C-termini (Cock and McCormick. 2001. *Plant Physiol.* 126: 939-942). Plant CLEs have been suggested to have roles in shoot, floral, and root meristem maintenance, organ size regulation, apical dominance, and vascular development (Casamitjana-Martinez et al. 2003. *Curr. Biol.* 13:1435-1441; Fiers et al. 2004. *Gene* 327:37-49; Fiers et al. 2005. *Plant Cell* 17:2542-2553; Hirakawa et al. 2008. *Proc. Natl. Acad. Sci. USA* 105:15208-15213; Hobe et al. 2003. *Dev. Genes Evol.* 213:371-381; Ito et al. 2006. *Science* 313:842-845; Strabala et al. 2006. *Cell* 100:635-644). To date, more than one hundred putative CLE genes have been identified from diverse plant species (Oelkers et al. 2008. *BMC Plant Biol.* 8:1.). Sequence alignments among plant CLE proteins reveal little sequence similarity outside their conserved CLE domains and mounting evidence implicates the conserved CLE domain as the major functional domain of CLE proteins (Fiers et al. 2005, 2006., supra; Hirakawa et al., supra; Ito et al., supra; Kondo et al. 2006. *Science* 313:845-848; Ni and Clark. 2006. *Plant Physiol.* 140:726-733). More recently, plant CLEs that encode multiple tandem C-terminal CLE motifs (Kinoshita et al. 2007. *Plant Cell Physiol.* 48: 1821-1825; Oelkers et al., supra) have been identified, although the biological significance of the repeated CLE motifs and the function of this novel class of plant CLE genes are yet to be discovered.

The *Arabidopsis* genome contains 32 CLE genes that encode CLE proteins with a single CLE motif located at or near their C-termini (Cock and McCormick, supra). The founding member, CLAVATA3 (CLV3), functions as a peptide ligand that interacts with the CLV1/CLV2 receptor complex to signal a stem cell restricting pathway in shoot and floral meristems (Fletcher et al. 1999. *Science* 283:1911-19). CLV1, expressed in the central zone of the shoot apical meristem (SAM), encodes a membrane-bound leucine-rich repeat receptor-like kinase (LRR-RLK; Clark et al. 1997. *Cell* 89:575-585). CLV2, having a much broader expression pattern than that of CLV1, encodes a LRR receptor-like protein lacking a kinase domain (Jeong et al. 1999. *Plant Cell* 11:1925-1933). The functional form of CLV3 is a 12-aa peptide derived from its CLE domain (Kondo et al., supra). The physical interaction between the dodeca-CLV3 peptide and the LRR domain of CLV1 was also demonstrated (Ogawa et al. 2008. *Science* 319:294). More recently, it was revealed that CORYNE (CRN), a novel receptor kinase, is a new component of the CLV3 signaling pathway in *Arabidopsis* (Muller et al. 2008. *Plant Cell* 20:934-946). The *Arabidopsis* WUSCHEL (WUS) gene, which encodes a homeodomain transcription factor, is also an important regulator that promotes stem cell identity in the SAM (Laux et al. 1996. *Development* 122:87-96; Mayer et al. 1998. *Cell* 95:805-815). WUS is a key target of the CLV signaling pathway and a negative regulatory feedback loop between WUS and CLV genes controls the size of the stem cell population in the SAM (Brand et al. 2000. *Science* 289:617-619; Schoof et al. 2000. *Cell* 100:635-644). Mutations in any of the CLV genes result in enlarged shoot and floral meristems due to the uncontrolled proliferation of stem cells (Clark et al. 1993. *Development* 119:397-418, Clark et al. 1995. *Development* 121:2057-2067; Fletcher et al, supra; Kayes and Clark. 1998. *Development* 125:3843-3851), whereas CLV3 overexpression or mutation of the WUS gene terminates SAM development (Brand et al. 2000, supra; Laux et al., supra).

Surprisingly, overexpression of a *H. glycines* CLE gene (Hg-4G12) in *Arabidopsis* caused premature termination of the SAM similar to CLV3 (Davis, in press; Wang et al. 2005. *Mol. Plant Pathol.* 6:187-191). In addition, the nematode CLE was able to rescue the *Arabidopsis* clv3-1 mutant phenotype when expressed under the control of the CaMV 35S promoter (Wang et al. 2005, supra). These results suggested that nematode and plant CLES share functional similarity and led to the hypothesis that ligand mimicry of plant CLE signaling peptides may be an important mechanism in cyst nematode parasitism of host plants (Mitchum et al., supra; Wang et al. 2005, supra).

Plant-mediated RNA interference (RNAi) has been used to target nematode parasitism genes and helped attain broad resistance against four root-knot nematode species in the model plant *Arabidopsis* (Huang et al. 2006. *Proc. Natl. Acad. Sci. USA* 103: 14302-14306). The double-stranded (dsRNA) or small interfering (siRNA) molecules were taken up by the nematode from soaking solution (in vitro) or from plant tissue (in planta). RNAi has been observed to function in both cyst and root-knot nematode species (Lilley et al. 2007. *Molecular Plant Path.* 8: 701-711). Production of parasite-specific dsRNA in plant cells has been suggested as a novel and durable strategy for control of plant parasitic nematodes including cyst nematodes (e.g. Gheysen and Vanholme. 2007. *Trends in Biotech.* 25: 89-92; Steeves et al. 2006. *Func. Plant Biol.* 33: 991-999; Sindhu et al. 2008. *Journal of Experimental Botany* 60:315-324; Patel et al. 2008. *Journal of Nematology* 40:299-310).

The use of nematode resistant cultivars is the most economical and environmentally-safe means of nematode control; therefore, there is a need for *G. rostochiensis*- and *G. pallida*-resistant cultivars.

SUMMARY OF THE INVENTION

We have cloned, sequenced, and characterized the function of five new CLAVATA3/ESR-related CLE genes from the potato cyst nematode *Globodera rostochiensis* and determined that four of the five Gr-CLE genes encode CLE proteins with multiple CLE motifs. We have confirmed their expression within the dorsal esophageal gland cell of nematode parasitic stages of *G. rostochiensis.*

In accordance with this discovery, it is an object of the invention to provide isolated novel nucleic acid compositions homologous to a portion of the CLE genes of *G. rostochiensis*, said compositions for controlling *G. rostochiensis* infection and parasitism of potatoes, tomatoes, and eggplants.

It is an additional object of the invention to provide a method for controlling the infection of a plant by a parasitic *G. rostochiensis* nematode, comprising the steps of contacting the nematode with a dsRNA molecule comprising one strand that is substantially identical to a portion of CLE gene, thereby controlling the infection of the plant by the *G. rostochiensis* nematode.

It is another object of the invention to provide a method for modifying or inhibiting the expression of the CLE gene in *G. rostochiensis* cells, the method comprising: transforming plant hairy roots with a vector comprising a nucleic acid sequence encoding a dsRNA operatively linked to a promoter and a transcription termination sequence, selecting for transformed plant hairy roots that have integrated the nucleic acid sequence into their genomes, screening the transformed plant hairy roots for expression of the dsRNA encoded by the nucleic acid sequence, and selecting plant hairy roots that express the dsRNA and/or siRNA.

It is an additional object of the invention to provide a double stranded ribonucleotide sequence produced by preparing a recombinant polynucleotide sequence comprising a first and a second polynucleotide sequence, wherein the first polynucleotide sequence comprises an isolated polynucleotide sequence homologous to a portion of said CLE-1 or CLE-4 gene of *G. rostochiensis*, wherein the second polynucleotide sequence is substantially the reverse complement of the first polynucleotide sequence such that the first and the second polynucleotide sequences hybridize when transcribed into a ribonucleic acid to form the double stranded ribonucleotide molecule. Inhibition of *G. rostochiensis* growth and development is accomplished by inhibiting expression of a nucleotide sequence in the *G. rostochiensis* that is complementary to the sequence of the first polynucleotide.

It is an additional object of the invention to provide a vector which comprises the construct which comprises the two polynucleotide sequences described above operably linked to a heterologous promoter functional in a plant cell.

It is another object of the invention to provide plant transformed by said vector, wherein said plants are potato, tomato, or eggplant.

It is yet another object of the invention to provide a strategy of developing *G. rostochiensis*-resistant potato cultivars.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 1A-1C depict the structure of Gr-CLE genes and relationship between nematode and plant CLE proteins. FIG. 1A, depicts the organization of Gr-CLE genes (drawn to scale) in comparison with CLV3. Exons and introns are indicated by boxes and solid lines, respectively. Numbers inside the boxes and below the lines indicate sizes (in base pairs) of exons and introns. Vertical lines indicate nucleotide differences in introns of Gr-CLE-4 genes in comparison with Gr-CLE-4-A. Gray boxes in the first exons indicate signal peptide (SP) and the black boxes in the last exons indicate the 12-amino acid (aa) CLE motifs. The numbers inside the black boxes and the letters in front of the black boxes indicate different CLE motifs and spacer sequences, respectively. FIG. 1B shows the alignments of GrCLE spacer sequences (left) and the putative 12-aa CLE domains of nematode and related *Arabidopsis* CLE proteins (right). Residues identical to those in the consensus sequences are shaded in black. The numbers above each alignment indicate positions relative to the first residue of the 12-aa CLE motif. The conserved hydrophobic residue at the −5 position is indicated by a triangle. FIG. 1C depicts the C-terminal sequence alignment of Gr-CLEs and plant CLEs with multiple CLE motifs. Residues identical to those in the consensus sequence are shaded in black. The −5 position relative to each CLE motif is indicated by an asterisk and each hydrophobic residue at the position is shaded in gray. Each CLE motif is numbered and marked by a thick line above the alignment. Proline-rich sequences are boxed. Genbank accession numbers for CLE proteins from

Figure 5:
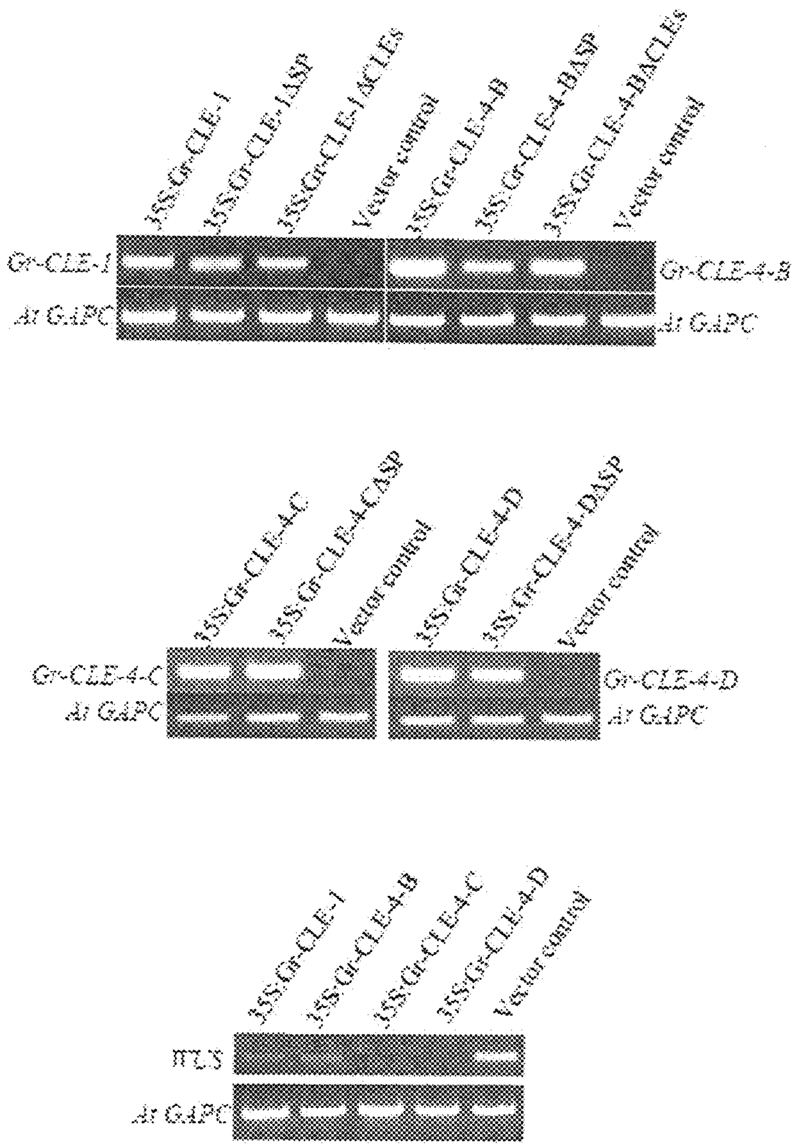

*Heterodera glycines* (Hg) 4G12, *Arabidopsis thaliana* (At) CLE1, CLE6, and CLV3 are AF473827, NP_683490, NP_565713, and Q9XF04, respectively; those for *Medicago truncatula* (Mt), *Oryza sativa* (Os), *Triticum aestivum* (Ta), and *Cyamopsis tetragonoloba* (Ct) are shown in FIG. 1C.

FIGS. 2A and 2B show the alignment of nematode and plant CLE proteins containing the putative SH3 domain interaction sequence in the variable domain. FIG. 2A shows the N-terminal sequence alignment of nematode CLE proteins. Amino acid residues corresponding to positions 1-144 of Gr-CLE-1 are shown. FIG. 2B shows the alignment of partial sequences of plant CLE proteins. Residues corresponding to positions 49-107 of At CLE10 are shown. In FIGS. 2A and 2B, residues identical or similar to those in the consensus sequences are shaded in black and gray, respectively. The putative SH3 domain interaction sequences are boxed and marked with the PXXP core motif. The signal peptide (SP) sequence and the 12-aa CLE motif are indicated by thick lines above the alignment. GenBank accession numbers for CLE proteins from *Heterodera glycines* (Hg) 4G12, *Arabidopsis thaliana* (At) CLE9 and CLE10, and *Oryza sativa* (Os) CLE104 and CLE508 are AF473827, NM_102422, DQ056515, AB332051, and AB332075, respectively; that for *Zea mays* (Zm) is shown in FIG. 2B.

FIGS. 3A and 3B depict spatial and developmental expression of Gr-CLE Genes. FIG. 3A depicts hybridization (dark staining; indicated by an arrow) of a digoxygenin-labeled antisense Gr-CLE-4 cDNA probe to mRNA expressed exclusively within the dorsal gland cell (DG) of a parasitic third-stage juvenile (par-J3) (upper panel) and a parasitic fourth-stage juvenile (par-J4) (lower panel) of *Globodera rostochiensis*. Bar=10 μm. S=stylet. FIG. 3B depicts developmental expression of Gr-CLE genes throughout the nematode life cycle. Each column represents the mean of two independent experiments with the standard deviations of the mean and each experiment contained three technical replicates for each mRNA sample. Tested stages included eggs, preparasitic second-stage juveniles (pre-J2), and parasitic J2s (par-J2), J3s (par-J3), and J4s (par-J4) within root tissues collected at 2, 5, 10, and 21 days post-inoculation (dpi).

FIGS. 4A-4H depict effects of synthetic CLE peptides on root growth and root meristem. FIGS. 4A and 4B depict the effects of different CLE peptides on the root growth of *Arabidopsis* (Columbia-0) and potato. The lengths of the main *Arabidopsis* roots were measured at 7, 10, and 13 days of growth on media containing individual peptides and the lengths of the main potato roots were measured at 7 and 10 days of growth on peptide-containing media. At least 24 *Arabidopsis* roots and 20 potato roots were included in each peptide treatment. Data and error bars represent mean±SD. Note that both *Arabidopsis* and potato roots treated with individual synthetic peptides of GrCLE1-1-12p, GrCLE1-1m-12p, GrCLE1-1-14p, GrCLE4-1-12p, GrCLE4-2-12p, and GrCLE4-3-12p were significantly shorter than roots with no peptide treatment or roots treated with the Ag-16p peptide ($P<0.01$, t test). Similar results were obtained from a second independent experiment. FIG. 4C-4G depict microscopic observation of the morphology of the primary roots of *Arabidopsis* (Columbia-0) 8 days after the treatment with different peptides. At least 10 roots treated with Ag-16p (FIG. 4D) or CLV3-12p (FIG. 4E) peptide and at least 18 roots under no peptide treatment (FIG. 4C) or treated with individual GrCLE peptides were microscopically examined. FIG. 4H shows consumption of *Arabidopsis* root meristem triggered by GrCLE peptides. The root apical meristem (RAM) regions of individual primary roots were measured microscopically. Note that the average size of root apical meristems of roots under no peptide treatment is significantly larger than those of root apical meristems of roots treated with GrCLE peptides ($P<0.001$, t test), revealing a consumption of root meristem in GrCLE peptide treated roots. In addition, the average size of root apical meristems of GrCLE1-1-12p treated roots is significantly less than those of root apical meristems of GrCLE4-1-12p ($P<0.01$, t test), GrCLE4-2-12p ($P<0.001$, t test), and GrCLE4-3-12p ($P<0.001$, t test) treated roots. The region of the RAM is marked by a bracket in FIGS. 4C to 4G. The bar in C=50 μm for FIGS. 4C to 4G.

FIG. 5 depicts the RT-PCR analysis of transgene, WUS gene, and an internal control gene (At GAPC) expression in shoot apical meristems (SAM) of transgenic *Arabidopsis* lines. Note that levels of WUS gene expression in the SAMs of transgenic lines overexpressing individual Gr-CLE genes were reduced compared to that of the vector control lines.

Figure 6P:
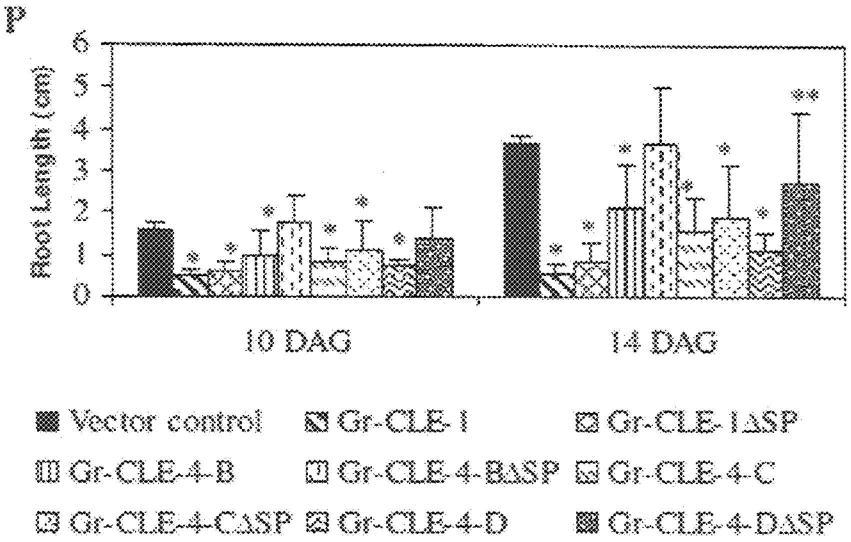

FIGS. 6A-6P show the phenotypes of *Arabidopsis* (Columbia-0) transgenic plants overexpressing individual Gr-CLE Genes. FIG. 6A shows an empty vector control plant 14 days after germination (DAG). FIG. 6B shows a 35S:Gr-CLE-1 plant at 14 DAG showing the suppression of the shoot apical meristem (SAM), anthocyanin accumulation, and dwarfism. FIG. 6C shows a 35S:Gr-CLE-4-8 plant at 14 DAG showing the SAM arrest. FIG. 6D shows a 35S:Gr-CLE-4-D plant at 14 DAG showing the SAM arrest. FIG. 6E shows an empty vector control plant at 21 DAG. FIG. 6F shows a 35S:Gr-CLE-1 plant at 21 DAG showing the SAM arrest, anthocyanin accumulation, and dwarfism. FIG. 6G shows a 35S:Gr-CLE-4-8 plant at 21 DAG showing the SAM arrest and the symptom of leaf yellowing. FIG. 6H shows a 35S:Gr-CLE-4-D plant at 21 DAG showing the emergence of a trumpet-shaped leaf. FIG. 6I shows a wild-type *Arabidopsis* flower containing four petals, six stamens, and two fused carpels. FIG. 6J shows a flower of a 35S:Gr-CLE-1 plant showing a decreased number of stamens and no carpels, a phenotype similar to that of a wus flower. FIG. 6K shows a 35S:Gr-CLE-1 flower with sepals and petals removed showing the shorter stamens. FIG. 6L shows a 35S:Gr-CLE-4-B flower with two stamens and no carpels. FIG. 6M shows transgenic plants expressing the empty vector control, 35S:Gr-CLE-1, 35S:Gr-CLE-4-B, 35S:Gr-CLE-4-C, and 35S:Gr-CLE-4-D, respectively (from left to right) at 50 DAG. Note that 35S:Gr-CLE-4-C and 35S:Gr-CLE-4-D plants exhibit very similar phenotypes. FIG. 6N shows a flower of a 35S:Gr-CLE-4-C plant with 5 stamens and no carpels. FIG. 6O shows an enlarged photo showing the 35S:Gr-CLE-4-B plant in M. Note that the plant exhibits the symptom of leaf yellowing. Bar in A=5 mm for A to H. Bar in I=1 mm for I to L and N. Bar in M=2 cm and bar in O=1 cm. FIG. 6P shows the lengths of the primary roots of transgenic *Arabidopsis* plants overexpressing individual Gr-CLE genes measured at 10 and 14 DAG. Between 36 and 70 roots of seedlings obtained from nine independent T1 pools for each genotype were analyzed. Note that the root lengths of all the transgenic lines except the 35S:Gr-CLE-4-BΔSP line are significantly shorter than those of the vector control line (* and **= $P<0.0001$ and $<0.001$, respectively, t test).

FIGS. 7A-7O depict that Gr-CLE genes provide partial or nearly complete rescue of clv3-2. FIG. 7A shows an enlarged inflorescence of a clv3-2 mutant. FIG. 7B shows a flower of a clv3-2 mutant carrying more floral organs in each whorl. FIG. 7C shows a silique of a clv3-2 mutant consisting of 6-7 carpels. FIG. 7D depicts inflorescence of a PCLV3:Gr-CLE-1/clv3-2 transgenic plant. Note that the size of the inflorescence is smaller than that of a clv3-2 mutant. FIG. 7E shows a flower of a PCLV3:Gr-CLE-1/clv3-2 transgenic plant showing a partial restoration of wild-type floral organ numbers.

FIG. 7F shows a silique of a PCLV3:Gr-CLE-1/clv3-2 transgenic plant showing a phenotype and a carpel number different from those of a clv3-2 silique. FIG. 7G depicts inflorescence of a PCLV3:Gr-CLE-4-B/clv3-2 transgenic plant showing a size similar to that of wild-type *Arabidopsis*. FIG. 7H shows a flower of a PCLV3:Gr-CLE-4-B/clv3-2 transgenic plant showing a complete restoration of wild-type floral organ numbers. FIG. 7I shows a silique of a PCLV3:Gr-CLE-4-B/clv3-2 transgenic plant consisting of 2 carpels. FIG. 6J depicts inflorescence of a PCLV3:Gr-CLE-4-C/clv3-2 transgenic plant showing a size similar to that of wild-type *Arabidopsis*. FIG. 7K shows a flower of a PCLV3:Gr-CLE-4-C/clv3-2 transgenic plant showing a partial restoration of wild-type floral organ numbers. FIG. 7L shows a silique of a PCLV3:Gr-CLE-4-C/clv3-2 transgenic plant showing a phenotype and a carpel number different from those of a clv3-2 silique. FIG. 7M depicts inflorescence of wild-type *Arabidopsis* (*Landsberg erecta*). FIG. 7N shows a wild-type *Arabidopsis* flower consisting of 4 petals, 6 stamens, and two fused carpels. FIG. 7O shows a silique of wild-type *Arabidopsis* consisting of two carpels. Bar in M=5 mm for A, D, G, J, and M. Bar in N=1 mm for B, E, H, K, and N. Bar in 0=5 mm for C, F, I, L, and O.

FIGS. 8A-8D depict Gr-CLE gene overexpression in potato hairy roots. FIG. 8A shows lengths of the primary roots of each transgenic potato hairy root line measured at 4, 6, 8, and 10 days after dissecting from the initial transgenic roots. Between 60 and 133 independent transgenic roots for each genotype were analyzed. Data and error bars represent mean±SD. Note that the root lengths of each transgenic line overexpressing individual Gr-CLE genes are significantly shorter than those of the vector control line (P<0.001, t test). FIG. 8B shows the morphology of an empty vector control root. FIG. 8C shows the morphology of a 35S:Gr-CLE-1 overexpressing hairy root showing the suppression of the root apical meristem (RAM) compared to the control root. FIG. 8D shows the morphology of a 35S:Gr-CLE-4-D overexpressing hairy root showing the suppression of the RAM. The region of the RAM is marked by a bracket in B to D. Bar in B=50 μm for B to D.

Figure 9:
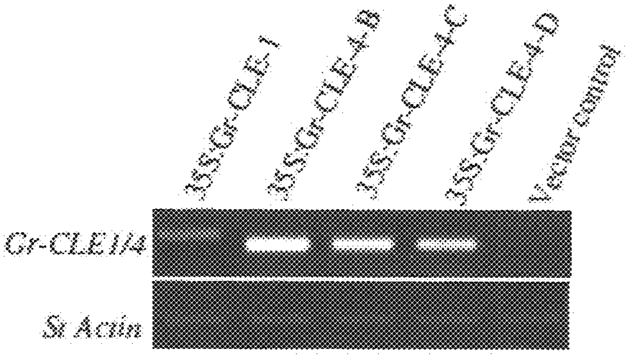

FIG. 9 depicts RT-PCR analysis of transgene expression in transgenic potato hairy root lines. Expression of the potato actin gene (St Actin) was used as an internal control.

Figure 10:

FIG. 10 is an illustration of the T-DNA region of the RNAi vector (pSUPERgus) containing the sense and antisense DNA fragment targeting a 423 bp of the Gr-CLE-1 gene or a 441 bp of the Gr-CLE-4 gene. The T-DNA region is inserted into the plant genome when plant is transformed with the vector.

Figure 11:
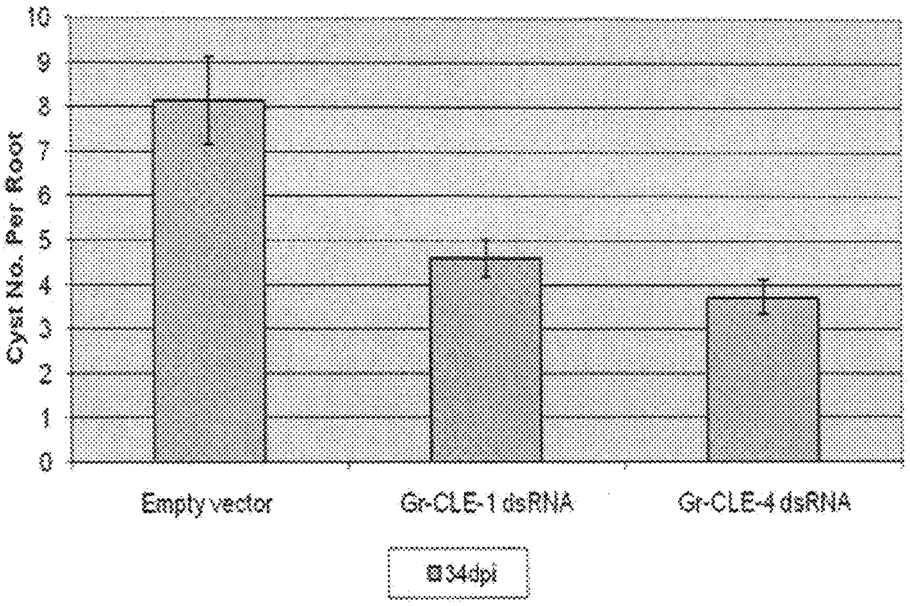

FIG. 11 shows the average number of cysts per root developed on transgenic lines expressing Gr-CLE-1 or Gr-CLE-4-B dsRNA or the empty RNAi vector at 34 days after inoculation of the second-stage juveniles of *G. rostochiensis.*

DETAILED DESCRIPTION OF THE INVENTION

We have identified and characterized the function of five CLE-like genes from *G. rostochiensis*. Unlike *H. glycines* CLEs, four of the five Gr-CLE-like genes were found to encode secreted proteins with multiple CLE motifs at their C-termini. Based on structure and sequence similarities, Gr-CLE genes were grouped into two classes: Gr-CLE-1 and Gr-CLE-4. These Gr-CLE genes were found to be exclusively expressed within the dorsal esophageal gland cell of nematode parasitic stages, indicating a potential role for these nematode secreted CLE proteins in plant parasitism. We also conducted detailed functional characterization of these Gr-CLE genes. Results from our in vitro and in planta studies demonstrate clearly that *G. rostochiensis* CLEs with either single or multiple CLE motifs can function as ligand mimics of plant CLE signaling peptides. Additionally, our in-depth functional characterization provides evidence to suggest that the evolution of multiple CLE motifs may be an important mechanism for generating functional diversity in CLE proteins to facilitate nematode parasitism. Furthermore, the discovery of CLE genes from a different genus of cyst nematodes signifies the importance of ligand mimicry as a mechanism for plant parasitism by this group of nematodes.

A common characteristic of the plant CLE family is that all members contain a conserved C-terminal CLE motif. The first non-plant CLE genes isolated from *H. glycines* also encode a single CLE motif at their C-termini (Gao et al., supra; Olsen and Skriver, supra; Wang et al. 2001, supra). Although several putative CLE genes encoding multiple CLE motifs have recently been identified from several plant species (Cock and McCormick, supra; Kinoshita et al., supra; Oelkers et al., supra), the biological significance of the multiple CLE motifs and function of this novel class of plant CLEs are unknown. In this study, we found that four of the five CLE genes identified from *G. rostochiensis* (Gr-CLE) encode multiple CLE motifs that are evenly separated by relatively conserved spacer sequences. The Gr-CLE genes encode four putative 12-aa CLE motifs that are organized in different combinations in Gr-CLE proteins, leading to a possibility of diversifying protein functions. Interestingly, our sequence analysis found that the residue at the −5 position upstream of the CLE motif in nematode and plant CLEs is usually hydrophobic. This residue may have an important role in CLE protein processing or function. Further sequence analysis identified a putative SH3 domain interaction site in the variable domain of nematode and several plant CLE proteins. SH3 domains are present in a variety of proteins and recognize proline-rich peptides (SH3 ligands) to mediate diverse cellular processes including signal transduction, cytoskeleton organization, and membrane trafficking (Cesareni et al. 2002. FEBBS Lett. 513: 38-44; Zarrinpar et al. 2003. Sci. STKE, RE8). Plant CLEs have been suggested to be C-terminally processed to release a functional CLE peptide (Kondo et al., supra; Ito et al., supra; Ni and Clark, supra). Thus, it is worthwhile to determine if nematode CLE proteins can be proteolytically processed in planta to release two functionally distinct peptides: a CLE ligand and a SH3 ligand. Although studies have indicated that the variable domain of CLV3 is dispensable for protein function (Fiers et al. 2006. *Plant Physiol.* 141:1284-1292.; Ni and Clark, supra), the identification of the conserved residues (Oelkers et al., supra and this study) and the SH3 domain interaction site indicates a need to further elucidate the biological importance of the variable domain of CLE proteins.

Accumulating evidence suggests that the conserved CLE motif is the major functional domain of plant CLE proteins. In this study, we provide three lines of evidence that Gr-CLE proteins with either single or multiple CLE motifs can function as ligand mimics of endogenous plant CLE peptides. First, exogenous application of synthetic GrCLE peptides to *Arabidopsis* and potato roots generated a short root phenotype similar to that caused by CLV3 and other plant CLE peptide treatments. Second, overexpression of Gr-CLE genes in *Arabidopsis* resulted in phenotypes closely resembling overexpression phenotypes reported for At CLE9, 10, 11, and 13 (Strabala et al., supra). Third, we found that the overexpressed Gr-CLE proteins could partially or completely replace the CLV3 function within meristems.

Like most *Arabidopsis* CLE peptides (Ito et al., supra; Kinoshita et al., supra), all of the synthetic GrCLE dodecapeptides suppressed *Arabidopsis* root growth in the in vitro root assay. It is worth mentioning that replacing the glycine residue at position 6 with alanine in the GrCLE1-1 peptide did not alter peptide activity, suggesting that unlike its role in CLV3 (Fletcher et al., supra), the glycine residue at position 6 may not be essential for nematode CLE peptide function. The GrCLE1-1 peptide caused a higher degree of root suppression in *Arabidopsis* than GrCLE4 peptides, and this was found to be consistent with the varying degrees of root suppression observed in *Arabidopsis* transgenic lines overexpressing Gr-CLE genes. Furthermore, the Gr-CLE-1 overexpressing line showed phenotypic differences from those of Gr-CLE-4 lines. Together, these results indicate that the Gr-CLE-1 protein or its processed peptide may signal through a receptor different from those of Gr-CLE-4 related peptides in *Arabidopsis*. It is intriguing that the longer peptide of GrCLE1-1-14p exhibited a comparable level of root suppression activity as GrCLE1-1-12p. Surprisingly, it was found that adding a single aa to the GrCLE4 dodecapeptides to make 13-aa peptides completely abolished peptide activities on root suppression. As suggested for plant CLEs, it is possible that the functional form of Gr-CLE-4 proteins may also be a dodecapeptide. However, considering that the in vitro root assay may not reflect in vivo activity of nematode CLE peptides and that it is still unclear if all plant CLE proteins are processed in a manner similar to CLV3 and Zinnia TDIF (Ito et al., supra; Kondo et al., supra), further in vivo assays are necessary to elucidate the nature and mechanism of the proteolytic processing of Gr-CLE proteins.

It has been suggested that it is the processed CLE peptide that interacts with its cognate receptor to mediate signal transduction. Overexpression of Gr-CLE genes in *Arabidopsis* resulted in wus-like seedlings, production of wus flowers, stunted roots, anthocyanin accumulation, delayed development, and death of young seedlings, many of which resembled overexpression phenotypes observed for *Arabidopsis* CLEs that contain only a single C-terminal CLE motif. Thus, our overexpression studies reveal that Gr-CLEs with either single or multiple CLE motifs can function similarly to plant CLEs and suggest that Gr-CLEs with multiple CLE motifs are proteolytically processed to release individual CLE peptides for function. Gr-CLEs have orderly arranged CLE motifs and they may become useful molecules for understanding the proteolytic processing of CLE proteins.

Many *Arabidopsis* CLEs are suggested to interact with similar receptors and play functionally redundant roles (Strabala et al., supra). Transgenic *Arabidopsis* lines overexpressing respective Gr-CLE-4-C and Gr-CLE-4-D genes resulted in very similar phenotypes. Dodecapeptides of GrCLE4-1 and GrCLE4-3 only differ in two residues. It is likely that Gr-CLE-4-C and Gr-CLE-4-D or their potentially released GrCLE4-1 and GrCLE4-3 peptides may have redundant functions. Gr-CLE-4-B has the potential to release three different 12-aa CLE peptides including GrCLE4-1, GrCLE4-2, and GrCLE4-3. The GrCLE4-2 dodecapeptide differs in four residues from GrCLE4-1 and in three residues from GrCLE4-3. The transgenic Gr-CLE-4-B line exhibited distinct differences in overexpression phenotypes from those of Gr-CLE-4-C and Gr-CLE-4-D lines. Additionally, Gr-CLE-4-B, but not Gr-CLE-4-C, was found to completely replace CLV3 activity when expressed in the stem cell domain. Together, these results reveal that Gr-CLE-4-B functions differently from Gr-CLE-4-C and Gr-CLE-4-D, providing the first evidence to suggest that the evolution of multiple CLE motifs may be an important mechanism for generating functional diversity in CLE proteins. *Arabidopsis* CLEs that have a stronger rescue of the clv3 mutant phenotype require CLV1 for function, whereas those that have partial or no rescue of clv3 act independently of CLV1 (Ni and Clark, supra). According to our prediction that GrCLE1-1 functions through a receptor different from those of GrCLE4 peptides and that GrCLE4-1 and GrCLE4-3 may function through similar receptors, it might be possible that it is the GrCLE4-2 peptide that acts through CLV1 to rescue clv3. CLV3 and At CLE1 and At CLE6 that provided nearly complete rescue of clv3-1 all contain an aspartic acid residue at position 8 within their respective CLE motifs. The GrCLE4-2 peptide also contains the same residue at position 8. As suggested by Ni and Clark (supra), this aspartic acid residue might be critical for CLV3 function.

Results from our overexpression studies suggest that like CLV3 (Rojo et al. 2002. Plant Cell 14: 969-977), Gr-CLEs may function extracellularly in planta and that nematode signal peptides are functional in *Arabidopsis* and can direct Gr-CLE proteins to the extracellular space for function. Intriguingly, however, *Arabidopsis* plants expressing individual Gr-CLE-4s that lack signal peptides exhibited similar phenotypes to those expressing full-length Gr-CLE-4 proteins. The predicted N-terminal signal peptides found on plant CLEs suggest that they function in the extracellular space, therefore, it is unlikely that nematode CLE mimics can exert their function in the cytoplasm. Thus, we interpret our results to suggest that Gr-CLEs without their respective signal peptides may still be secreted to some extent. One possibility is that constitutive high level of expression of Gr-CLEs results in some protein leakage; although constitutive overexpression of CLV3 without its signal peptide did not cause any observable phenotypes in *Arabidopsis* (Rojo et al., supra). Another possibility is that the variable domain, the function of which remains unknown, plays a role in extracellular targeting of nematode CLE proteins. Future studies to monitor protein targeting will need to be undertaken to address the latter possibility.

Potato, but not *Arabidopsis*, is a host for *G. rostochiensis*. A short root phenotype similar to that observed in *Arabidopsis* was revealed when synthetic GrCLE peptides were applied exogenously to potato roots or when Gr-CLE genes were overexpressed in potato hairy roots, suggesting that conserved CLE signaling components that have a role in controlling root growth may exist in both *Arabidopsis* and potato. Several putative CLE genes have been identified in the potato genome (Oelkers et al., supra). In addition, results from in vitro and in vivo studies in potato support our hypothesis that the cognate receptor in potato that interacts with Gr-CLE-1 or its processed peptide may be different from those that interact with Gr-CLE-4 related peptides. With the completion of the potato genome, we anticipate that additional CLE genes and CLV-related or RLK genes involved in CLE signaling will be discovered in potato. Because of the conservation of CLE signaling components observed between *Arabidopsis* and potato, in vitro receptor screening using *Arabidopsis* mutants may help identify orthologous nematode CLE receptors in potato.

It is becoming increasingly evident that nematode gland secretions play a direct role in regulating host cellular processes involved in the induction, formation, and maintenance of the syncytium (Davis et al. 2004, 2008, supra). The discovery of the first non-plant CLE genes from *H. glycines* and associated functional characterization has led to the hypothesis that CLE proteins secreted by the nematode function as ligand mimics of plant CLE signaling peptides to directly manipulate plant developmental pathways for the dedifferentiation of root cells to form a syncytium (Mitchum et al., supra; Wang et al., supra). This hypothesis is further supported by recent evidence that signaling in *Arabidopsis* shoot and root meristems is regulated by conserved factors (Sarkar et al. 2007. *Nature* 446: 811-814) including a CLV-like pathway for root meristem maintenance (Casamitjana-Martinez et al., supra) and that both CRN and CLV2 mediate CLE signaling in *Arabidopsis* roots (Fiers et al., supra; Muller et al., supra). Consistent with this hypothesis, a recent study has demonstrated that RNAi silencing of CLE genes from *H. glycines* affects the parasitic success of the nematode (Bakhetia et al. 2007. *Mol. Plant Microb Interact.* 20: 306-312).

Gr-CLE genes are exclusively expressed within the dorsal esophageal gland cell of parasitic stages of the nematode. Although both classes of Gr-CLE genes were upregulated during nematode parasitism, they showed different expression patterns during the parasitic life cycle; Gr-CLE-1 was upregulated in the early parasitic stages with a level much lower than that of Gr-CLE-4 genes and declined in later parasitic stages, whereas Gr-CLE-4 genes were dramatically upregulated in early parasitic stages and remained high in later parasitic stages. The different expression patterns observed between Gr-CLE-1 and Gr-CLE-4 genes may suggest different functions of their gene products in plant parasitism, consistent with our prediction that Gr-CLE-1 may interact with a plant receptor different from those of Gr-CLE-4 proteins. Unlike *H. glycines* which usually selects root cells with meristematic potential for syncytium formation (Endo, B. Y. 1964. *Phytopathology* 54: 79-88; Endo, B. Y. 1991. *Rev. Nematol.* 14: 73-94), *G. rostochiensis* initiates a syncytium preferentially from a fully differentiated cortical cell (Jones and Northcote, supra). It is likely that simultaneous stimulation of multiple CLE signaling pathways may be necessary for the establishment and maintenance of the syncytium. Significantly, it was recently revealed that plant CLE peptides from two functional classes act synergistically to suppress differentiation and promote auxin-mediated proliferation of vascular cells in *Arabidopsis* (Whitford et al. 2008. *Proc. Natl. Acad. Sci. USA* 105: 18625-18630). Auxin has been shown to involve in the induction and development of the syncytium (Goverse et al. 2000. *Mol. Plant-Microbe Interact.* 13: 1121-1129; Karczmarek et al. 2004. *Mol. Plant Pathol.* 5: 343-346). It would be interesting to determine if the two classes of Gr-CLE genes encode for antagonistic or synergistic functions and if there is a potential interplay between auxin and nematode CLE-mediated actions in syncytium formation.

The present invention may be used to reduce crop destruction by the parasitic cyst nematode *Globodera rostochiensis.*

The nucleic acid molecules, constructs and vectors of the invention and the methods of using them can be utilized to induce resistance to *G. rostochiensis* in important food crops. We have used RNAi-based technology to generate nematode-resistant hairy roots. Such technology can be used to generate nematode-resistant plants as a strategy to provide broad resistance in potato plants against *Globodera* pests.

RNA interference (RNAi) is a process utilizing endogenous cellular pathways whereby a double stranded RNA (dsRNA) specific target gene results in the degradation of the mRNA of interest. In recent years, RNAi has been used to perform gene silencing in a number of species and experimental systems, from the nematode *C. elegans*, to plants, to insect embryos and cells in tissue culture (Fire et al. 1998. *Nature* 391: 806-811; Martinez et al. 2002. *Cell* 110: 563-574; McManus and Sharp. 2002. *Nat. Rev. Genet.* 3: 737-747). RNAi works through an endogenous pathway including the Dicer protein complex that generates about 20-25-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knock-down or silencing of mRNA expression is usually sequence specific. The gene silencing effect of RNAi persists for days and, under experimental conditions, can lead to a decline in abundance of the targeted transcript of 90% or more, with consequent decline in levels of the corresponding protein.

In accordance with the invention, a parasitic *G. rostochiensis* nematode is contacted with a dsRNA, which specifically inhibits expression of the target gene CLE-1 or CLE-4, which is essential for survival, infection and parasitism of host plants. Preferably, the parasitic *G. rostochiensis* nematode comes into contact with the dsRNA after entering a plant, which expresses the dsRNA. In one embodiment, the dsRNA is encoded by a vector, which has been transformed into an ancestor of the infected plant. Preferably, the nucleic acid sequence expressing said dsRNA is under the transcriptional control of a root specific promoter.

Accordingly, the dsRNA of the invention is substantially identical to a portion of the CLE-1 or CLE-4 target gene of the *G. rostochiensis* genome. Preferably, the dsRNA of the invention comprises (a) a first strand comprising a sequence that is substantially identical to from about 21 to about 423 (CLE-1) or 441 (CLE-4) consecutive nucleotides of the CLE-1 or CLE-4 target gene and (b) a second strand comprising a sequence substantially complementary to the first strand.

Fragments of dsRNA larger than about 21 nucleotides in length are cleaved intracellularly by plants to siRNAs of about 21 nucleotides in length, and these siRNAs are the actual mediators of the RNAi phenomenon. Example 9 demonstrates that siRNAs are generated when a vector containing the *G. rostochiensis* CLE-1 or CLE-4 target gene is transformed into potato hairy roots. The cyst count is reduced when *G. rostochiensis* is inoculated onto transgenic potato hairy roots expressing a dsRNA comprising one strand that is identical to a portion of the *G. rostochiensis* CLE-1 or CLE-4 target gene, as compared to a *G. rostochiensis*-inoculated transgenic control hairy root line that contains the empty vector and does not contain a dsRNA comprising one strand that is substantially identical to a portion of the *G. rostochiensis* CLE-1 or CLE-4 target gene. Thus the dsRNA of the present invention may range in length from about 21 nucleotides to about 423 or 441 nucleotides.

dsRNA containing a nucleotide sequence identical to a portion of the *G. rostochiensis* CLE-1 or CLE-4 target gene is preferred for inhibition. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for inhibition. Thus, sequence identity may be optimized by sequence comparison and alignment algorithms known in the art. Thus, the determination of percent identity between any two sequences can be accomplished using a mathematical algorithm. Non-limiting examples of such mathematical algorithms are the algorithm of Myers and Miller (1988. *CABIOS* 4: 11-17), the local homology algorithm of Smith et al. (1981. *Adv. Appl. Math.* 2: 482); the homology alignment algorithm of Needleman and Wunsch (1970. *J. Mol. Biol.* 48: 443-453); the search-for-similarity-method of Pearson and Lipman (1988. *Proc. Natl. Acad. Sci.* 85: 2444-2448; the algorithm of Karlin and Altschul (1990. *Proc. Natl. Acad. Sci. USA* 87: 2264), modified as in Karlin and Altschul (1993. *Proc. Natl. Acad. Sci. USA* 90: 5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Greater than 90% sequence identity, or even 100% sequence identity, between the inhibitory RNA and the portion of the CLE-1 or CLE-4 target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 21, 25, 50, 100, 200, 300, 400, or 423 (for CLE-1) or 441 (for CLE-4) bases. In a preferred embodiment, the length of the double-stranded nucleotide sequence is from approximately from about 21 to about 423 (CLE-1) or 441 (CLE-4) nucleotides in length.

Preferably, the dsRNA molecule of the present invention comprises one strand comprising a sequence substantially identical to a portion of the CLE-1 or CLE-4 target gene from *G. rostochiensis.*

The dsRNA of the invention may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Higher doses of double-stranded material may yield more effective inhibition.

In another embodiment, the invention provides an isolated recombinant expression vector comprising a nucleic acid encoding a dsRNA molecule as described above, wherein expression of the vector in a host plant cell results in increased resistance to *G. rostochiensis* as compared to a wild-type variety of the host plant cell. As used herein, the term “vector” refers to a nucleic acid molecule capable of transporting another nucleic acid to which it has been linked. One type of vector is a “plasmid,” which refers to a circular double stranded DNA loop into which additional DNA segments can be ligated. Another type of vector is a viral vector, wherein additional DNA segments can be ligated into the viral genome. Certain vectors are capable of autonomous replication in a host plant cell into which they are introduced. Other vectors are integrated into the genome of a host plant cell upon introduction into the host cell, and thereby are replicated along with the host genome. Moreover, certain vectors are capable of directing the expression of genes to which they are operatively linked. Such vectors are referred to herein as “expression vectors.” In general, expression vectors of utility in recombinant DNA techniques are often in the form of plasmids. In the present specification, “plasmid” and “vector” can be used interchangeably as the plasmid is the most commonly used form of vector. However, the invention is intended to include such other forms of expression vectors, such as viral vectors (e.g., potato virus X, tobacco rattle virus, and Geminivirus), which serve equivalent functions.

The recombinant expression vectors of the invention comprise a nucleic acid of the invention in a form suitable for expression of the nucleic acid in a host plant cell, which means that the recombinant expression vector includes one or more regulatory sequences, selected on the basis of the host plant cells to be used for expression, which is operatively linked to the nucleic acid sequence to be expressed.

In accordance with the invention, the recombinant expression vector comprises a regulatory sequence operatively linked to a nucleotide sequence that is a template for one or both strands of the claimed dsRNA. In one embodiment, the nucleic acid molecule further comprises a promoter flanking either end of the nucleic acid molecule, wherein the promoters drive expression of each individual DNA strand, thereby generating two complementary RNAs that hybridize and form the dsRNA. In another embodiment, the nucleic acid molecule comprises a nucleotide sequence that is transcribed into both strands of the dsRNA on one transcription unit, wherein the sense strand is transcribed from the 5' end of the transcription unit and the antisense strand is transcribed from the 3' end, wherein the two strands are separated by 3 to 500 base pairs, and wherein after transcription, the RNA transcript folds on itself to form a hairpin. In accordance with the invention, the spacer region in the hairpin transcript may be any DNA fragment.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and be transiently expressed or transiently active. Whether present in an extra-chromosomal non-replicating vector or a vector that is integrated into a chromosome, the polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals.

In accordance with the present invention, the expression cassette comprises an expression control sequence operatively linked to a nucleotide sequence that is a template for one or both strands of the dsRNA. The dsRNA template comprises (a) a first stand having a sequence substantially identical to from about 21 to about 423 (CLE-1) or 441 (CLE-4) consecutive nucleotides of SEQ ID NO: 1 or SEQ ID NOs: 3-6; and (b) a second strand having a sequence substantially complementary to the first strand. In further embodiments, a promoter flanks either end of the template nucleotide sequence, wherein the promoters drive expression of each individual DNA strand, thereby generating two complementary RNAs that hybridize and form the dsRNA. In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by 3 to 500 base pairs, and wherein after transcription, the RNA transcript folds on itself to form a hairpin.

The invention is also embodied in a transgenic plant capable of expressing the dsRNA of the invention and thereby inhibiting the CLE-1 or CLE-4 target gene in *G. rostochiensis*. Suitable methods for transforming or transfecting host cells including plant cells can be found in Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. Any method may be used to transform the recombinant expression vector into plant cells to yield the transgenic plants of the invention.

In accordance with this embodiment, the transgenic plant of the invention is produced by a method comprising the steps of providing a *G. rostochiensis* CLE-1 or CLE-4 gene, preparing an expression cassette having a first region that is substantially identical to a portion of the CLE-1 or CLE-4 gene and a second region which is complementary to the first region, transforming the expression cassette into a plant, and selecting progeny of the transformed plant which express the dsRNA construct of the invention.

Increased resistance to *G. rostochiensis* infection is a general trait wished to be inherited into a wide variety of plants, including but not limited to potato, tomato, and eggplant. In a preferred embodiment, the plant is a potato plant.

Preferably, the dsRNA of the invention is introduced into parasitic *G. rostochiensis* when the nematodes ingest transgenic plants containing expression vectors encoding the dsRNA.

As used herein, the term "amount sufficient to inhibit expression" refers to a concentration or amount of the dsRNA that is sufficient to reduce levels or stability of mRNA of CLE-1 or CLE-4 produced from CLE-1 or CLE-4 target gene in a parasitic *G. rostochiensis* nematode. As used herein, "inhibiting expression" refers to the absence or observable decrease in the level of protein and/or mRNA product from the CLE-1 or CLE-4 target gene. Inhibition of the CLE-1 or CLE-4 target gene expression may be lethal to the parasitic *G. rostochiensis* nematode, or such inhibition may delay or prevent entry into a particular developmental step (e.g., metamorphosis), if plant disease is associated with a particular stage of the parasitic nematode's life cycle. The consequences of inhibition can be confirmed by examination of the outward properties of the nematode (as presented below in Example 5).

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. supra. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the CLE-1 or CLE-4 gene, operably linked to a promoter and/or other regulatory sequences.

As used herein, the term "express" or "expression" is defined to mean transcription alone. The regulatory elements are operably linked to the coding sequence of the CLE-1 or CLE-4 gene such that the regulatory element is capable of controlling expression of CLE-1 or CLE-4 gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence which specifically induces the CLE-1 or CLE-4 gene expression in roots. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

As used herein, the term "expressed sequence tag" (EST) refers to a short strand of DNA (approximately 200 base pairs long) which is part of a cDNA. ESTs provide an indication of the abundance of the genes that are being expressed in that tissue at that stage of development. Because an EST is usually unique to a particular cDNA, and because cDNAs correspond to a particular gene in the genome, ESTs can be used to help identify unknown genes and to map their position in the genome.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. 1987. *Meth. Enzymol.* 143: 277) and particle-accelerated or "gene gun" transformation technology (Klein et al. 1987. *Nature* (London) 327: 70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to the CLE-1 or CLE-4 polypeptide that is substantially free of other proteins, lipids, carbohydrates or other materials with which it is naturally associated. One skilled in the art can purify CLE-1 or CLE-4 using standard techniques for protein purification. The purity of the CLE-1 or CLE-4 polypeptide can also be determined by amino-terminal amino acid sequence analysis.

The invention includes functional CLE-1 or CLE-4 polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of CLE-1 or CLE-4 polypeptide", refers to all fragments of CLE-1 or CLE-4 that retain CLE-1 or CLE-4 activity. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of CLE-1 or CLE-4 can be utilized in bioassays to identify functional fragments of the CLE-1 or CLE-4 polypeptide or related polypeptides.

Modifications of the CLE-1 or CLE-4 primary amino acid sequence may result in further mutant or variant proteins having substantially equivalent activity to the CLE-1 or CLE-4 polypeptides described herein. Such modifications may be deliberate, as by site-directed mutagenesis, or may occur by spontaneous changes in amino acid sequences where these changes produce modified polypeptides having substantially equivalent activity to the CLE-1 or CLE-4 polypeptides. Any polypeptides produced by minor modifications of the CLE-1 or CLE-4 primary amino acid sequence are included herein as long as the biological activity of CLE-1 or CLE-4 is present.

A heterologous coding sequence refers to coding sequences which encode peptides or proteins, unrelated to, or, other than, the CLE-1 or CLE-4 polypeptides provided above and which are not intrinsically found in the position provided in the chimeric gene construct.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a CLE-1 or CLE-4 polypeptide and which hybridize under stringent conditions, as described herein, to the CLE-1 or CLE-4 sequences disclosed herein, or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art, as discussed above.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48: 443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular nematode protein. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the CLE-1 or CLE-4 polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, CLE-1 or CLE-4 activity as described herein. Such variants may result from, for example, genetic polymorphism or from human manipulation. Biologically active variants of a native CLE-1 or CLE-4 protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired CLE-1 or CLE-4 activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of CLE-1 or CLE-4 protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful cloning of CLE-1 and CLE-4 genes is a major step in identifying and understanding the regulatory mechanisms underlying resistance to the potato cyst nematode in plants. Deciphering the mechanism by which this gene functions to result in *G. rostochiensis*- and *G. pallida*-resistant cultivars will aid in devising new strategies and/or control points for eradicating *G. rostochiensis* and *G. pallida* in crops.

EXAMPLES

Having now generally described this invention, the same will be better understood by reference to certain specific examples, which are included herein only to further illustrate the invention and are not intended to limit the scope of the invention as defined by the claims.

Example 1

Nematode Culture and Inoculation

The potato cyst nematode (*G. rostochiensis*) (pathotype R01) was propagated on greenhouse-grown susceptible potato (*Solanum tuberosum* cv. Katandin; Brodie et al. 1991. *Amer. Potato J.* 68:1-11) and cysts were extracted as described previously (Brodie, B. B. 1996. *J. Nematol.* 28:510-519). Cysts were soaked in distilled water for seven days and crushed to release the eggs. Infective second-stage juveniles (J2) were collected by hatching eggs in potato root diffusate (Clarke and Perry. 1977. *Nematologica* 23:350-368) and used for inoculation on monoxenic potato root cultures to obtain nematode-infected root materials as described previously (Lu et al. 2008. *Mol. Biochem. Parasit.* 162:1-15). Root segments collected at 2 and 5 days post-inoculation (dpi) were found to contain nematodes mainly at the parasitic J2 stage, and root segments collected at 10 and 21 dpi were found to contain nematodes mostly at parasitic J3 and J4 stages, respectively. These infected roots were used as parasitic nematode materials for detecting Gr-CLE gene expression using the quantitative real-time reverse transcription-PCR (qRT-PCR) assay described below. Mixed parasitic stages of the nematode were extracted from infected potted plants (Wang et al. 2001, supra) and used for in situ mRNA hybridization analysis.

Example 2

Nucleic Acid Isolation

For mRNA isolation, frozen packed rehydrated cysts, preparasitic J2s or infected potato root segments were transferred into a Lysing Matrix D tube containing 1.4 mm ceramic spheres (Qbiogene, Carlsbad, Calif., USA) and homogenized using a Mini-Beadbeater-8 Cell Disrupter (BioSpec Products, Bartlesville, Okla., USA). The homogenized material was then used for mRNA extraction using the Dynabeads mRNA DIRECT Kit (Invitrogen, Carlsbad, Calif., USA) following the manufacturer's instructions. 30-50 ng of mRNA was used for first-strand cDNA synthesis. For nematode genomic DNA isolation, packed preparasitic J2s (−100 μl) were resuspended in 0.5 ml of lysis buffer containing 100 mM NaCl, 100 mM Tris-HCl, pH 8.0, 50 mMEDTA, pH 8.0, 1% SDA. 1% β-mercaptoethanol, and 100 μg/ml proteinase K (Invitrogen) and incubated at 65° C. for 30 min. Nematode DNA was extracted from the lysed mixture by phenol, phenol/chloroform (1:1), and chloroform extractions, then precipitated with ethanol.

Example 3 cDNA and Genomic Cloning

*H. glycines* CLE protein sequences (Gao et al., supra; Wang et al. 2001, supra) were used to search the NematodeNet EST database (retrieved from the Internet: <URL: www.nematode.net) using the TBLASTN program (Altschul et al. 1997. *Nucleic Acids Res.* 25:3389-3402) and an EST from a cDNA library of *G. rostochiensis* was identified to have similarity to the CLE motif of *H. glycines* CLEs. A partial sequence of the target gene (named Gr-CLE-1) was cloned by PCR using primers of GR02145-48F and GR02145-605R and the first-strand cDNA obtained from preparasitic J2s as template. A 5' RACE procedure (Invitrogen) was then used to obtain the rest of the 5' untranslated region (UTR) of the gene. The full-length cDNA sequence of Gr-CLE-1 (SEQ ID NO: 1) was finally obtained by PCR using primers of CLE1-5UTRF1 and AUAP (Invitrogen). The full-length cDNA sequence of Gr-CLE-1 was found to encode a predicted protein of 204 amino acids that contained a putative N-terminal signal peptide (FIG. 1A) analyzed by the SignalP program (Nielsen et al. 1997). Interestingly, unlike *H. glycines* CLEs that contain only one C-terminal CLE motif, Gr-CLE-1 was found to contain four putative CLE motifs at its C-terminus (FIG. 1A); this unique structure which is absent from the 32-member *Arabidopsis* CLE family has only been identified in a very few putative CLEs from rice and other plant species (Kinoshita et al. 2007; Oelkers et al. 2008). The last motif (GrCLE1-2, RVTPGVPDRQHR) was dissimilar to the first three identical CLE motifs (GrCLE1-1, RVTPGGPDPLHN). Within the conserved 12-aa CLE motifs of plant CLEs, residues at positions 1, 4, 6, 7, 8, 9, 11, and 12 are highly conserved (Oelkers et al. 2008). The GrCLE1-2 motif contained four residue differences with GrCLE1-1 at positions 6, 9, 10, and 12 (FIG. 1B). Only two putative plant CLE motifs of At CLE43 and Pc CLE178 have an arginine residue instead of a conserved proline residue at position 9 and none of the plant CLE motifs identified has an arginine residue at position 12 (Oelkers et al. 2008). It is possible that GrCLE1-2 may not be a functional CLE motif. Noticeably, the last three motifs of Gr-CLE-1 were each preceded by a 9-aa spacer (named GrCLE1-a and GrCLE1-b) containing 7-8 polar residues and one central hydrophobic residue (leucine) located 5 aa (designated as position −5) upstream of the first residue of the following 12-aa CLE motif (FIG. 1B). The 9-aa sequence (GrCLE1-a') preceding the first GrCLE1-1 motif was divergent from the other spacers, but retained a hydrophobic residue (tyrosine) at the −5 position (FIG. 1B). The variable domain between the signal peptide and the start of the first GrCLE1-1 motif had little sequence similarity to known proteins in the databases and was only about 27% identical to those of *H. glycines* CLEs.

Primers of CLE1-5UTRF1 and CLE1-3UTRR2 were used for amplifying the corresponding genomic sequence of Gr-CLE-1 (SEQ ID NO: 2) from the *G. rostochiensis* genomic DNA. The genomic clone of Gr-CLE-1 was revealed to contain two introns (FIG. 1A) similar to that observed in the CLV3 (FIG. 1A) and the At CLE40 genes (Fletcher et al. 1999; Hobe et al. 2003).

Further analysis of about 100 cDNA clones obtained by RT-PCR using mRNA isolated from preparasitic J2 or nematode-infected root materials identified four additional CLE-like genes. Additional Gr-CLE genes (named Gr-CLE-4s) were obtained by PCR using primers of CLE1-ATGF and CLE1-TGAR and the first strand cDNA obtained from preparasitic J2s or from nematode-infected root materials as template. The 3'-end UTRs of Gr-CLE-4 genes were obtained by 3'RACE using primer CLE4-359F designed according to the conserved internal regions of Gr-CLE-4 genes and the AUAP primer (Invitrogen). The 5'-end UTRs of Gr-CLE-4 genes were obtained by 5'RACE using primer CLE4-c265R pr CLE4-c103R designed according to the conserved N-terminal regions of Gr-CLE-4 genes and the AAP primer (Invitrogen). Full-length Gr-CLE-4 cDNAs were then obtained by PCR using primer pair of CLE4-5UTR1F and AUAP (Invitrogen) or primer pair of CLE4-5UTR1F and CLE4-3UTR1R. Although variations existed, these CLE-like genes were 90-99% identical to each other and only 72-78% identical to Gr-CLE-1. Therefore, these four CLE-like genes were grouped into a separate class from Gr-CLE-1 and subsequently designated as Gr-CLE-4-A, Gr-CLE-4-B, Gr-CLE-4-C, and Gr-CLE-4-D (FIG. 1A). In addition, our cloning and sequence analysis showed that the relative abundance of the mRNA transcripts of Gr-CLE-4 genes varied significantly with Gr-CLE-4-B and Gr-CLE-4-C representing the most abundant transcripts in both preparasitic and parasitic stages of the nematode. However, transcripts of Gr-CLE-4-A and Gr-CLE-4-D were found only in the preparasitic J2 and parasitic stages, respectively, revealing a low expression of Gr-CLE-4-A and Gr-CLE-4-D in certain stages of nematode development. A total of four different Gr-CLE-4 genes named Gr-CLE-4-A (SEQ ID NO: 3), Gr-CLE-4-B (SEQ ID NO: 4), Gr-CLE-4-C (SEQ ID NO: 5), and Gr-CLE-4-D (SEQ ID NO: 6) were obtained. The genomic clones of Gr-CLE-4 genes were obtained using primer pairs of CLE4-5UTR1F and CLE4-3endR2 (for Gr-CLE-4-A; SEQ ID NO: 7), CLE4-5UTR17F and CLE4-3endR2 (for Gr-CLE-4-B; SEQ ID NO: 8), or CLE4-5UTR1F and 31506C3-3UTR1R (for Gr-CLE-4-C, SEQ ID NO: 9 and Gr-CLE-4-D, SEQ ID NO: 10) designed respectively to the corresponding cDNA sequences.

All the amplified PCR products were cloned into the pCRII-TOPO vector (Invitrogen) and sequenced at the Cornell University Life Sciences Core Laboratories Center.

The deduced Gr-CLE-4 proteins also contained an N-terminal signal peptide, a variable domain, and a C-terminal region that contained either single or multiple CLE motifs (FIG. 1A). The variable domains of Gr-CLE-4 proteins were 65-67% identical to that of Gr-CLE-1 and only 24-27% identical to those of *H. glycines* CLEs. All Gr-CLE-4 proteins except Gr-CLE-4-C had either four or five tandem CLE motifs at their C-termini with the potential to produce three different 12-aa CLE peptides (FIGS. 1A and B) if proteolytically processed in vivo as suggested for plant CLEs (Ito et al. 2006; Kondo et al. 2006; Ni and Clark 2006). Similar to Gr-CLE-1, the CLE motifs of Gr-CLE-4-A, Gr-CLE-4-B, and Gr-CLE-4-D were each preceded by a 9-aa conserved spacer (named GrCLE4-a through GrCLE4-f) that contained a hydrophobic residue (leucine or phenylalanine) at the −5 position (FIG. 1B). The 9-aa sequences (GrCLE4-a) preceding the first CLE motif of each Gr-CLE-4 protein were identical. Interestingly, the hydrophobic nature of the residue at the −5 position was relatively conserved in plant CLEs that contain multiple CLE motifs (FIG. 1C) as well as in plant CLEs containing a single CLE motif.

All Gr-CLE-4 genes contained two introns (FIG. 1A). The second introns among Gr-CLE-4 genes were almost identical whereas their first introns were relatively polymorphic (FIG. 1A). The genomic clones of Gr-CLE-4 genes were only about 73% identical to that of Gr-CLE-1.

Gr-CLE proteins contain a putative SH3 interaction domain sequence in their variable domains. Plant CLEs have very little sequence similarity except for the conserved C-terminal CLE domain. However, the amino acid alignment of nematode CLE proteins showed a conserved proline-rich region in their variable domains (FIG. 2A). Interestingly, proline-rich sequences were also found in the spacer regions of several plant CLEs that contain multiple CLE motifs (FIG. 1C). Proline-rich sequences may interact with proline recognition domains including the SH3 (Src homology 3), WW, EVH1, and GYF domains to mediate diverse intracellular signaling processes (Hou et al. 2006; Zarrinpar et al. 2003). The SH3 domain is probably the best-characterized structural unit found in numerous signaling proteins and they often recognize proline-rich peptides with the conserved core motif of PXXP (P represents proline and X represents any amino acid) that forms a left-handed polyproline type II helix (Zarrinpar et al. 2003). By using the SH3-Hunter (retrieved from the Internet: <URL (cbm.bio. uniroma2.it/SH3-Hunter/; Ferraro et al. 2007), a web server for predicting putative SH3 domain interaction sites on protein sequences, we found that the proline-rich sequences present in the variable domains of nematode CLEs except Gr-CLE-1 may resemble SH3 ligands that contain the PXXP core motif (FIG. 2A). Putative SH3 domain interaction sequences containing the PXXP core motif were also identified in the variable domains of several plant CLE proteins (FIG. 2B).

Example 4

In Situ mRNA Hybridization

Primers of CLE1-3UTRF2, CLE1-3UTRR2, CLE4-273F, and CLE4-349R were used to synthesize digoxigenin (DIG)-labeled sense and antisense cDNA probes of Gr-CLE-1 and Gr-CLE-4, respectively, using the PCR DIG Probe Synthesis Kit (Roche Applied Science, Indianapolis, Ind., USA) by asymmetric PCR (Wang et al. 2001, supra). Parasitic stages of the nematode were fixed, permeabilized and used for in situ mRNA hybridization as described (De Boer et al. 1998. *J. Nematol.* 30:309-312; Wang et al. 2001, supra). cDNA probes that hybridized within nematode specimens were detected by alkaline phosphatase-conjugated anti-DIG antibody, BCIP-NBT substrate staining, and compound light microscope observation.

Gr-CLE genes are gland-specific and differentially expressed throughout the nematode life cycle. We used in situ mRNA hybridization to determine the spatial expression pattern of Gr-CLE genes in nematode specimens. Hybridization results using a Gr-CLE-4 probe that could also potentially recognize Gr-CLE-1 showed a strong hybridization signal specifically within the dorsal esophageal gland cell of parasitic stages of the nematode (FIG. 3A). A very weak hybridization signal was also detected within the dorsal gland cell of parasitic nematodes using a Gr-CLE-1 specific cDNA probe (data not shown). The presence of a putative signal peptide and the gland-specific expression suggest a role for Gr-CLE proteins in plant parasitism.

Example 5

Developmental Expression Profiling

The quantitative real-time PCR (qPCR) TaqMan assay was used to quantify the expression of Gr-CLE-1 and Gr-CLE-4 genes throughout the nematode life cycle. The *G. rostochiensis* β-actin gene (Gr-act-1; GenBank accession no. EF437156) was used as an endogenous reference for all cDNA samples tested. Primers CLE1-85F and CLE1-209R and probe CLE1-c152F which specifically hybridize to Gr-CLE-1 were used to detect Gr-CLE-1 transcripts. Primers CLE4-42F and CLE4-166R and probe CLE4-c120F which specifically hybridize to Gr-CLE-4 were used to detect Gr-CLE-4 transcripts. Primers GrActin-c660Fb and GrActin-R2b and probe GrActin-c880F were used to detect Gr-act-1 transcripts. CLE1-c125F, GrCLE4-c120F, and GrActin-c880F were designed to span exon-exon junctions in the fully processed transcripts of the target genes to prevent hybridization to any potential contaminating genomic DNA in the samples. The specificity of each primer/probe pair was confirmed using corresponding cDNA and genomic DNA clones of Gr-CLE genes as well as plant cDNA as templates. The qRT-PCR assay was carried out in an iCycler iQ Real-Time PCR Detection System (Bio-Rad Laboratories, Hercules, Calif., USA) as previously described (Lu et al., supra). The mRNA sample for each developmental stage was prepared from two independent experiments and used for cDNA synthesis. All qRT-PCR assays consisted of three technical replicates for each mRNA sample. Data was analyzed using the iCycler iQ Real-Time PCR Detection System Software version 3.0a (Bio-Rad). Gr-CLE-1 and Gr-CLE-4 expression levels were calculated using the comparative $C_t$ ($2^{-\Delta\Delta C_t}$) method following a standard protocol (User Bulletin 2, ABI PRISM 7700 Sequence Detection System; Applied Biosystems, Foster City, Calif., U.S.A). For each developmental stage, $2^{-6\Delta\Delta C_t}$ represented the amount of the target transcript that was normalized to an endogenous reference (Gr-act-1) and relative to a calibrator that had a lowest expression of the target gene at the preparasitic J2 stage. All TaqMan probes that contained a fluorescence reporter dye (6-carboxyfluorescein or FAM) and a quencher dye (6-carboxy-tetramethyl-rhodamine or TAMRA) respectively at their 5' and 3' ends were synthesized by Integrated DNA Technology (Coralville, Iowa, U.S.A).

TaqMan qRT-PCR was used to determine the expression profiles of Gr-CLE-1 and Gr-CLE-4 genes throughout the nematode life cycle. Infected roots that contained nematodes at different developmental stages were used as parasitic nematode materials for qRT-PCR analysis. Gr-CLE-1 and Gr-CLE-4 genes were revealed to have different expression patterns although both of them were found to be up-regulated in nematode parasitic stages (FIG. 3B). In the early parasitic stages, e.g., at 2, 5, and 10 days post inoculation (dpi), transcripts of Gr-CLE-1 increased gradually and reached the highest level at 10 dpi; an 8-fold increase in expression compared to the preparasitic J2 stage. Gr-CLE-4 had a much higher expression level than Gr-CLE-1 throughout the parasitic stages. Compared to preparasitic J2, transcripts of Gr-CLE-4 had a 200- to 500-fold increase in the early parasitic stages (5 and 10 dpi) and a more than 1200-fold increase at 21 dpi. Since the Gr-CLE-4 TaqMan probe could recognize all of the Gr-CLE-4 genes, it is not clear if the difference in expression level is related to a difference in gene copy number between the two classes of Gr-CLE genes or is a reflection of a difference in promoter activities of the Gr-CLE-1 and Gr-CLE-4 genes. The expression of both Gr-CLE-1 and Gr-CLE-4 genes was low in the preparasitic life stages including eggs and preparasitic J2s (FIG. 3B).

Example 6

Effect of Synthetic GrCLE Peptides on *Arabidopsis* and Potato Roots

Mounting evidence supports that the conserved CLE motif represents the major functional domain of plant CLE proteins. Gr-CLE genes encode four different 12-aa CLE motifs (FIG. 1A). To examine the functional sufficiency of these nematode CLE motifs, we conducted in vitro root assays (Fiers et al. 2005) using synthetic dodecapeptides (GrCLE1-1-12p, GrCLE4-1-12p, GrCLE4-2-12p, and GrCLE4-3-12p) corresponding to the four CLE motifs of Gr-CLE proteins. A 16-aa peptide (Ag-16p) (Fiers et al. 2005) corresponding to the C-terminus of AGAMOUS that has no similarity with plant CLE motifs and a 12-aa CLV3 peptide (CLV3-12p) were used as negative and positive controls, respectively. In addition, several peptides, including a mutated GrCLE1-1 dodecapeptide (GrCLE1-1m-12p, with a Gly-to-Ala conversion as in clv3-1 and clv3-5 mutants), a 14-aa GrCLE1-1 peptide (GrCLE1-1-14p, with one additional N-terminal and one additional C-terminal residue compared to Gr-CLE1-1-12p), and three 13-aa peptides of GrCLE4-1-13p, GrCLE4-2-13p, and GrCLE4-3-13p (all contained an extra N-terminal lysine residue compared to the corresponding dodecapeptides), were synthesized and used in the in vitro root assays.

Peptides with a purity of >70% were synthesized (Sigma-Aldrich Corp., St. Louis, Mo., U.S.A) and dissolved in filter-sterilized 50 mM sodium phosphate buffer. Three Gr-CLE-1 related peptides were synthesized: GrCLE1-1-12p (12 aa, RVIPGGPDPLHN; SEQ ID NO: 12), GrCLE1-1m-12p (12 aa, RVIPGAPDPLHN; SEQ ID NO: 13, with a G-to-A conversion at position 6), and GrCLE1-1-14p (14 aa, KRVIPGGPDPLHNR; SEQ ID NO: 14). Six Gr-CLE-4 related peptides were synthesized: GrCLE4-1-12p (12 aa, RVAGAGPDPIHH; SEQ ID NO: 15), GrCLE4-1-13p (13 aa, KRVAGAGPDPIHH; SEQ ID NO: 16), GrCLE4-2-12p (12 aa, RAVPAGPDPKHH; SEQ ID NO: 17), GrCLE4-2-13p (13 aa, KRAVPAGPDPKHH; SEQ ID NO: 18), GrCLE4-3-12p (12 aa, RGAPAGPDP IHH; SEQ ID NO: 19), and GrCLE4-3-13p (13 aa, KRGAPAGPDPIHH; SEQ ID NO: 20). Positive and negative control peptides included CLV3-12p (12 aa, RTVPSGPDPLHH; SEQ ID NO: 21) and Ag-16p (16 aa, APNNHHYSSAGRQDQT; SEQ ID NO: 22) (Fiers et al., 2005).

For peptide treatments, seeds of wild-type *Arabidopsis* (Columbia-0) and potato, nonhost and host of *G. rostochiensis*, respectively, were surface-sterilized and plated on square plates (8-12 seeds per plate) containing the assay medium (Fiers et al. 2005, supra) with 10 μM of each peptide. Assay plates were placed vertically in a growth chamber and cultured at 23° C. for 16 h of light and 8 h of dark. The root length was measured from the base of the hypocotyl to the tip of the primary root at several time points after plating. Two independent experiments were conducted.

The CLV3-12p peptide severely suppressed root growth of both *Arabidopsis* (FIG. 4A) and potato (FIG. 4B) as compared with the no peptide or the Ag-16p peptide treatment. As observed previously with the 14-aa CLV3 peptide (Fiers et al. 2005), *Arabidopsis* roots treated with CLV3-12p showed a phenotype of root meristem consumption (FIG. 4E) compared with the control roots (FIGS. 4C and D). All of the dodecapeptides of GrCLE1-1-12p, GrCLE4-1-12p, Gr-CLE4-2-12p, and GrCLE4-3-12p suppressed root growth when applied exogenously to *Arabidopsis* and potato roots, but to varying degrees (FIGS. 4A and B). GrCLE1-1-12p had a comparable level of suppression as CLV3-12p on both *Arabidopsis* and potato roots. However, the three dodecapeptides of GrCLE4 showed a lesser degree of root suppression compared with GrCLE1-1-12p, especially on potato roots. Interestingly, we found that the mutated GrCLE1-1m-12p peptide gave a similar level of suppression as GrCLE1-1-12p on both *Arabidopsis* (FIG. 4A) and potato roots (FIG. 4B). Consistent with the root phenotype observed for the CLV3 peptide treatment, *Arabidopsis* roots treated with GrCLE peptides also showed a phenotype of root meristem consumption; however, the degree of root meristem consumption was more severe for roots treated with GrCLE1-1-12p than for those treated with GrCLE4 peptides (FIGS. 4F, G, and H).

Since a processed 12-aa CLE peptide has been suggested to interact with its plant receptor (Ito et al. 2006; Kondo et al. 2006; Ogawa et al. 2008), we investigated the potential functional forms of Gr-CLE proteins by examining the activity of synthetic peptides that contained extra residue(s) in addition to the 12-aa CLE motifs. Surprisingly, GrCLE1-1-14p showed a similar level of activity as GrCLE1-1-12p on the suppression of both *Arabidopsis* and potato root growth (FIGS. 4A and B). In contrast, the longer peptides of GrCLE4-1-13p, GrCLE4-2-13p, and GrCLE4-3-13p did not show activities on root suppression (FIGS. 4A and B).

To examine root meristems, primary root tips were excised from peptide treated *Arabidopsis* seedlings or from transgenic potato hairy roots and immediately mounted in water onto a glass slide. Roots were examined under an Olympus BX-50 microscope equipped with Nomarski optics and images were captured using a QImaging Retiga EXi digital CCD camera (QImaging, Surrey, BC, Canada). The root apical meristem (RAM) regions of individual primary roots that covered the distance from the position around the quiescent center to the position where elongated root cells immediately follow cytoplasm-dense meristematic cells were measured microscopically. The collected data were analyzed using the MetaMorph imaging analysis software (Universal Imaging Corporation, Downingtown, Pa., U.S.A.)

Example 7

Transgene Constructions and Plant Transformations

For overexpression studies, Gr-CLE genes were subcloned into the pMD1 vector (Tai et al. 1999.) under the control of the CaMV 35S promoter. To generate 35S:Gr-CLE-1, 35S:Gr-CLE-1ASP, and 35S:Gr-CLE-1ΔCLE constructs, primer pairs of CLE1-spF and CLE1-TGAxhoR, CLE1-nospF and CLE1-TGAxhoR, and CLE1-spF and CLE1-mTAGxhoR were used respectively to amplify the corresponding coding regions from Gr-CLE-1. To generate similar constructs for Gr-CLE-4 genes, primer pairs of CLE4B1-spF and 4B1-TGAxhoR, CLE4B1-nospF and 4B1-TGAxhoR, and CLE4B1-spF and 4B1-mTAGxhoR were used for amplifying the corresponding sequences from Gr-CLE-4-8 and Gr-CLE-4-C, respectively. The same sets of primer pairs were also used for generating Gr-CLE-4-D constructs except that the CLE4B1-spF primer was replaced with the CLE1-spF primer because the signal peptide sequence of Gr-CLE-4-D was identical to that of Gr-CLE-1. Each amplified PCR product was cloned into pMD1 at the BamHI and XhoI sites. The resulting constructs were transformed individually into the *Agrobacterium tumefaciens* strain GV3101 and wild-type *Arabidopsis* (Columbia-0) plants were transformed using the *A. tumefaciens*-mediated floral dip method (Clough and Bent. 1998.).

Overexpression of Gr-CLE genes in *Arabidopsis* produces phenotypes resembling plant CLE genes. *Arabidopsis* CLE overexpression phenotypes have been characterized into distinct groups including Ai) aboveground wus phenotypes and short roots, Aii) aboveground wus phenotypes and long roots, B) dwarf, C) shrub-like, and D) long root (Strabala et al. 2006). Overexpression of the *H. glycines* CLE gene, Hg-4G12, in *Arabidopsis* produced phenotypes similar to *Arabidopsis* CLEs that fall into the Ai subgroup which includes At CLE9, 10, 11, and 13 (Wang et al. 2005). Unlike *H. glycines* CLEs, Gr-CLE proteins except Gr-CLE-4-C contained multiple CLE motifs. To gain insight into the potential function of Gr-CLE proteins in planta, we conducted overexpression studies in *Arabidopsis*, a nonhost for *G. rostochiensis*. In addition to discovering overexpression phenotypes, we wanted to determine the potential site of action of Gr-CLE proteins in vivo, and to confirm the functional importance of nematode CLE domains. Therefore, for each Gr-CLE gene, three different expression constructs were generated: full-length coding sequence; the coding sequence without the signal peptide; and the coding sequence lacking the CLE domain. Each gene was cloned behind the CaMV 35S promoter and the resulting construct (e.g., 35S:Gr-CLE-1, 35S:Gr-CLE-1ΔSP, or 35S:Gr-CLE-1ΔCLE) was introduced into wild-type *Arabidopsis*. For each genotype, between 52 and 199 primary transgenic plants that were obtained from nine independent T1 pools were analyzed. Transgene expression was confirmed by RT-PCR (FIG. 5). Since the Gr-CLE-4-A gene is very similar to the Gr-CLE-4-B gene, an overexpression study was not conducted for Gr-CLE-4-A.

For detecting the expression of transgenes in transgenic *Arabidopsis* lines, primer pairs of CLE1-c127F and CLE1-415R and CLE4-273F and CLE4-c265R were used for detecting the expression of Gr-CLE-1 and Gr-CLE-4 genes, respectively. The primer pair of AtGAPC-F and AtGAPC-R was used for examining the expression of the glyceraldehyde-3-phosphate dehydrogenase C subunit gene (At GAPC) (NM_111283). mRNA was extracted from the shoot apical meristems of young *Arabidopsis* seedlings and used for cDNA synthesis. The PCR cycling conditions were 94° C. for 40 s, followed by 25 (for the At GAPC gene) or 30 (for Gr-CLE genes) cycles of 94° C. for 40 s, 60° C. for 40 s, 72° C. for 1 min, and a final reaction of 72° for 10 min.

Of the 125 transgenic 35S:Gr-CLE-1 plants examined, one hundred percent produced a wus-like phenotype where the SAM ceased normal organ initiation after the generation of the first true leaves (FIG. 6B). These plants had much smaller rosette diameters at 14 days after germination (DAG) (FIG. 6B) compared to the empty-vector controls (FIG. 6A) and remained dwarf at later developmental stages (FIGS. 6F and M). 35S:Gr-CLE-1 plants generally showed elevated anthocyanin accumulation (FIGS. 6B, F, and M). Forty-nine percent of the wus plants were not able to recover from the initial SAM arrest and died before they flowered (Table 1). The rest of the wus plants that survived produced abnormal flowers, some of which lacked carpels and had a decreased number of stamens (similar to wus flowers; Laux et al., supra; FIG. 6J) and some had shorter stamens (FIG. 6K) compared to wild-type flowers (FIG. 6I). Roots of transgenic 35S:Gr-CLE-1 plants were severely stunted (FIG. 6P), consistent with the short root phenotype of *Arabidopsis* roots treated exogenously with the GrCLE-1-1 peptides. In addition, under the long-day conditions used in the experiments, transgenic 35S:Gr-CLE-1 plants displayed delayed development; e.g., the average time to the first floral bud (stage 5.10; Boyes et al. 2001) was 52 DAG compared to 24 DAG for the vector controls (Table 1).

Of the 169 transgenic 35S:Gr-CLE-1ΔSP plants analyzed, only 29% displayed a wus-like phenotype (Table 1) and most of them produced normal flowers later on. The rest of the 35S:Gr-CLE-1ΔSP plants showed no obvious aboveground phenotypes although most of them had comparable levels of transgene expression as those of 35S:Gr-CLE-1 plants (FIG. 5). Interestingly, 35S:Gr-CLE-1ΔSP roots were also stunted compared to the vector controls (FIG. 6P); however, the degree of root stunting was less severe than that of 35S:Gr-CLE-1 roots. Although transgene expression was confirmed (FIG. 5), plants expressing 35S:Gr-CLE-1ΔCLEs showed no obvious phenotypes (Table 1), indicating that the CLE motifs of Gr-CLE-1 were necessary for function.

TABLE 1

Phenotypes of transgenic *Arabidopsis* plants overexpressing Gr-CLE genes.

| Construct | # Plants Anal. | % wus-like | % Dwarf | Antho-cyanin | % Mortality | Flower Pheno-types | Time to Stage 5.10 (DAG)[a] |
|---|---|---|---|---|---|---|---|
| 35S:Gr-CLE-1 | 125 | 100 | 100 | Yes | 49 | wus; those with shorter stamens | 52 |
| 35S:Gr-CLE-1ΔSP | 169 | 29 | 18 | No | 17 | Mostly wild-type | 34 |
| 35S:Gr-CLE-1ΔCLEs | 131 | 0 | 0 | No | 1 | Wild-type | 25 |
| 35S:Gr-CLE-4-B | 85 | 100 | 0 | No | 73 | wus | 50 |
| 35S:Gr-CLE-4-BΔSP | 199 | 82 | 0 | No | 22 | wus and wild-type | 35 |
| 35S:Gr-CLE-4-B ΔCLEs | 136 | 0 | 0 | No | 2 | Wild-type | 26 |
| 35S:Gr-CLE-4-C | 81 | 98 | 0 | No | 21 | Mostly wus | 46 |
| 35S:Gr-CLE-4-CΔSP | 65 | 92 | 0 | No | 7 | Mostly wus | 44 |
| 35S:Gr-CLE-4-C ΔCLEs | 52 | 0 | 0 | No | 13 | Wild-type | 29 |
| 35S:Gr-CLE-4-D | 188 | 100 | 0 | No | 3 | Mostly wus | 58 |
| 35S:Gr-CLE-4-DΔSP | 216 | 98 | 0 | No | 2 | Mostly wus | 37 |
| 35S:Gr-CLE-4-D ΔCLEs | 78 | 0 | 0 | No | 9 | Wild-type | 28 |
| Empty Vector Control | 60 | 0 | 0 | No | 6 | Wild-type | 24 |

[a]DAG = days after germination

One hundred percent of 35S:Gr-CLE-4-B transgenic plants also displayed wus-like phenotypes including the suppression of the SAM at an early developmental stage (FIG. 6C) and the production of wus flowers (FIG. 6L) later on. Most plants showed symptoms of leaf yellowing or plant death by 3 weeks after germination (FIG. 6G). Seventy-three percent of the wus plants never recovered from the initial SAM arrest and died early (Table 1). Plants that did survive continued to show poor growth and symptoms of leaf yellowing (FIGS. 6M and O). Unlike 35S:Gr-CLE-1 overexpressing plants, 35S:Gr-CLE-4-B plants did not display dwarfism at early developmental stages and had no obvious anthocyanin accumulation (FIGS. 6C and G). 35S:Gr-CLE-4-B roots exhibited a short root phenotype, but the degree of root suppression was much less than that observed in 35S:Gr-CLE-1 roots (FIG. 6P). Similar to 35S:Gr-CLE-1 plants, 35S:Gr-CLE-4-B transgenic plants also displayed delayed development having an average time to stage 5.10 at 50 DAG (Table 1). Overexpression phenotypes including generation of wus seedlings, production of wus flowers, and developmental delay were also observed in 35S:Gr-CLE-4-BΔSP overexpressing plants (Table 1), but 35S:Gr-CLE-4-BΔSP plants did not show an altered root growth (FIG. 6P). Levels of transgene expression were comparable between 35S:Gr-CLE-4-8 and 35S:Gr-CLE-4-BΔSP transgenic plants (FIG. 5). In general, 35S:Gr-CLE-4-BΔSP transgenic plants showed relatively milder phenotypes than those of 35S:Gr-CLE-4-8 plants. As observed for 35S:Gr-CLE-1ΔCLEs plants, 35S:Gr-CLE-4-BΔCLEs plants did not display obvious phenotypes (Table 1).

Comparable degrees of phenotypes were observed between 35:Gr-CLE-4-C and 35:Gr-CLE-4-CΔSP transgenic plants and between 35S:Gr-CLE-4-D and 35S:Gr-CLE-4-DΔSP transgenic plants. In general, Gr-CLE-4-C and Gr-CLE-4-D overexpressing plants exhibited very similar phenotypes including generation of wus seedlings, production of wus flowers, developmental delay, and altered root growth (FIG. 6D, M, N, P, and Table 1). In addition, Gr-CLE-4-C and Gr-CLE-4-D plants often produced trumpet-shaped leaves (FIG. 6H). It is worth noting that among all the transgenic lines tested, 35S:Gr-CLE-4-D plants displayed the most delayed development having an average time of 58 DAG to reach stage 6.10 (Table 1). Consistent with the finding for Gr-CLE-1 and Gr-CLE-4-B proteins, the CLE motifs of Gr-CLE-4-C and Gr-CLE-4-D were necessary for function as no obvious phenotypes were observed in 35S:Gr-CLE-4-CΔCLEs and 35S:Gr-CLE-4-DΔCLEs transgenic plants (Table 1).

All of the transgenic lines expressing individual full-length Gr-CLE genes that showed wus-like phenotypes were found to have decreased levels of WUS expression in the SAM compared to the vector control lines (FIG. 5), indicating a functional similarity of Gr-CLE proteins to CLV3.

Example 8

Complementation

Gr-CLE proteins can completely or partially replace CLV3 activity within meristems. For the complementation study, Gr-CLE genes were subcloned into pBU14 under the control of the CLV3 promoter (Brand et al. 2002. *Plant Physiol.* 129:565-575). To generate the PCLV3:Gr-CLE-1 construct, primer pair of CLE1-spF and CLE1-TGAxbaR was used. To generate PCLV3:Gr-CLE-4-B and PCLV3:Gr-CLE-4-C constructs, primer pair of CLE4B1-spF and 4B1-TGAxbaR was used. Each amplified PCR product was cloned into pBU14 at BamHI and XbaI sites. *Arabidopsis* clv3-2 mutant plants were transformed with *A. tumefaciens* GV3101 harboring each of the above constructs.

All transformants were selected on ½×MS medium containing 50 μg/mL of kanamycin (Sigma-Aldrich) (for the pMD1 vector) or 30 μg/mL of glufosinate ammonium (Fisher, Pittsburgh, Pa., U.S.A.) (for the pBU14 vector) and transgenic *Arabidopsis* plants were then cultivated at 24° C. for 16 h of light and 8 h of dark in a growth room. For measuring the root growth rate, transgenic plants expressing individual Gr-CLE genes or the empty vector were first selected on kanamycin containing medium for five days, then transferred to ½×MS plates and cultured vertically at 24° C. for 16 h of light and 8 h of dark in a growth chamber (Percival, Perry, Iowa, U.S.A.).

Several plant CLEs have been shown to be able to replace CLV3 function when expressed in the stem cell domain (Hobe et al. 2003; Ni and Clark 2006). Gr-CLE-1, Gr-CLE-4-B, and Gr-CLE-4-C were the most representative Gr-CLE genes identified. To determine if these genes could replace CLV3 activity in the shoot and floral meristems, the full-length sequences of these three genes were cloned under the control of the CLV3 promoter and introduced into *Arabidopsis* clv3-2 mutant plants. clv mutants have enlarged shoot and floral meristems that lead to shoot fasciation and formation of extra floral organs including an increase in carpel number (Clark et al. 1993, 1995; Kayes and Clark 1998). For example, flowers of a clv3-2 mutant usually have six to seven carpels in the fourth whorl (Clark et al. 1995), whereas wild-type flowers have only two carpels in the fourth whole. Carpel number is a sensitive measurement for meristem size (Clark et al. 1993; Ni and Clark 2006). Multiple independent transgenic lines for each transgene were obtained and analyzed (Table 2). Significantly, Gr-CLE-4-B was found to provide nearly complete rescue of the clv3-2 meristem defects, resulting in plants that displayed a similar size of the floral meristem (FIG. 7G) as that of wild-type *Arabidopsis* (FIG. 7M) and produced flowers (FIG. 7H) and siliques (FIG. 7I) that contained an average of two carpels similar to those of wild-type *Arabidopsis* (FIGS. 7N and O). Gr-CLE-1 and Gr-CLE-4-C genes could also provide partial rescue of clv3-2, resulting in plants that had a decreased size of the floral meristem (FIGS. 7D and J) compared to that of clv3-2 (FIG. 7A) and produced flowers (FIGS. 7E and K) and siliques (FIGS. 7F and L) that contained an average of three to four carpels different from those of clv3-2 (FIGS. 7B and C). Together, these results indicate that Gr-CLE proteins can activate the CLV3 signaling pathway when expressed in the stem cell domain.

TABLE 2

Gr-CLE genes provide partial or nearly complete rescue of clv3-2.

| Construct | Number of transgenic plants showing Rescue of the clv3-2 mutant: Partial | Nearly Complete | # Analyzed Plants[a] |
|---|---|---|---|
| PCLV3:Gr-CLE-1 | 4 | 0 | 6 |
| PCLV3:Gr-CLE-4-8 | 0 | 21 | 21 |
| PCLV3:Gr-CLE-4-C | 8 | 0 | 8 |

[a]Plants obtained from 6 to 9 independent T1 pools were analyzed.

Example 9

Overexpression of Gr-CLE Genes in Potato Hairy Roots

*A. rhizogenes* strain 15834 was transformed with individual transgene constructs of interest and used for the generation of potato hairy roots as described previously (Wang et al. 2007. *Mol. Plant Pathol.* 8:423-436) with some modifications. Potato stem pieces from tissue cultures were incubated with the transformed *A. rhizogenes* cell suspension for 10 mins, then transferred onto the callus induction medium containing 1×MS salts (Sigma-Aldrich), 26.7 μM Glycine, 4 μM Nicotinic Acid, 2.4 μM Pyridoxine HCL (Sigma-Aldrich), 1.2 μM Thiamine HCL (Sigma-Aldrich), 0.5 μM Folic Acid, 0.2 μM d-biotin (Sigma-Aldrich), 0.01% Myo-inositol (Acros, Morris Plains, N.J., U.S.A.), 3% sucrose, 0.001% 6-BAP (Sigma-Aldrich), 0.002% NAA (Sigma-Aldrich), and 1% agar and cultivated for four days at 24° C. without light. The infected stem pieces were then cultured on the propagation medium containing 1×MS salts, 1.2 mM NaH2PO4, 0.01% Myo-inositol, 0.1% Thiamine HCl, 3% sucrose, 1% agar, 50 μg/mL of kanamycin, and 238 μg/mL of timentin (GlaxoSmithKline). Timentin was used to inhibit the growth of *A. rhizogenes* 15834 and kanamycin was added to select for transformed roots. Approximately 12-15 days after root emergence, 1 cm-long root tips were dissected and cultured on vertical plates containing the propagation medium with 119 μg/mL of timentin and the root growth rate was measured at different time points.

A short root phenotype was observed when individual Gr-CLE genes were overexpressed in *Arabidopsis*, a nonhost of *G. rostochiensis*. To evaluate if Gr-CLE genes could function similarly in potato, a host of *G. rostochiensis*, transgenic potato hairy roots overexpressing individual Gr-CLE genes were generated and analyzed. Similar to the effects in *Arabidopsis*, the overexpressed Gr-CLE-1, Gr-CLE-4-B, Gr-CLE-4-C, and Gr-CLE-4-D proteins could generate a short root phenotype in potato hairy roots (FIG. 8A). Furthermore, as observed in *Arabidopsis* roots, transgenic potato hairy roots overexpressing Gr-CLE-1 were much shorter than those overexpressing individual Gr-CLE-4 genes (FIG. 8A). A close examination of these short roots revealed a phenotype of root meristem consumption (FIGS. 8C and D) because root hairs of these short roots were formed much closer to the tips than those of the control roots expressing only the empty vector (FIG. 8B). Transgene expression in potato hairy roots was confirmed by RT-PCR analysis (FIG. 9).

Example 10

RNA Interference (RNAi)

We have cloned parasitism genes, Gr-CLE-1 (GenBank accession numbers EU386829 (cDNA sequence) and EU386830 (genomic DNA sequence), and Gr-CLE-4s (GenBank accession numbers EU386833 for Gr-CLE-4-A cDNA sequence and EU386840 for Gr-CLE-4-A genomic DNA sequence, EU386834 for Gr-CLE-4-B cDNA sequence and EU386841 for Gr-CLE-4-B genomic DNA sequence, EU386836 for Gr-CLE-4-C cDNA sequence and EU386843 for Gr-CLE-4-C genomic DNA sequence, and EU386837 for Gr-CLE-4-D cDNA sequence and EU386844 for Gr-CLE-4-D genomic DNA sequence. These genes were found to be highly expressed within the dorsal gland cell of the nematode. In addition, our in-depth functional characterization revealed that Gr-CLE-1 and Gr-CLE-4s encoded products can function as ligand mimics of plant CLE signaling peptides suggesting that ligand mimicry may be an important mechanism for *G. rostochiensis* to parasitize host plants. We have also cloned a homologue (Gp-CLE-1) of Gr-CLE-1 from *G. pallida*. Together, our results suggested that these parasitism genes may play critical roles in plant parasitism by potato cyst nematodes. Due to the importance of these nematode parasitism genes in plant parasitism, silencing of these parasitism genes has the potential to generate enhanced or broad resistance to the two species of the potato cyst nematode in transgenic potatoes.

RNA interference (RNAi) is a gene silencing process triggered by double-stranded RNA (dsRNA). Recent work has demonstrated that the expression in a host plant of dsRNA targeting an essential nematode parasitism gene resulted in broad resistance to root knot nematode infection. This plant-derived RNAi approach represents a viable means of developing broad or increased resistance to cyst nematodes as well.

Transgenic potato hairy roots expressing the RNAi construct targeting the Gr-CLE-1 or Gr-CLE-4gene were generated. Approximately 40 transgenic hairy root lines were obtained for each construct. About 10 transgenic potato hairy lines expressing only the empty vector were obtained and used as a negative control. Approximately 50 infective second-stage juveniles of *G. rostochiensis* were inoculated on each transgenic root line grown in the petri-dish and female numbers were counted at 34 days after inoculation.

The average number of cysts developed on transgenic root lines expressing Gr-CLE-1 or Gr-CLE-4 dsRNA was about 4 per root (FIG. 11), whereas the average number of cysts developed on transgenic root lines expressing only the empty vector was about 8 per root (FIG. 11). These results revealed a approximately 50% reduction in the average number of females per root in the Gr-CLE-1 or Gr-CLE-4 dsRNA transgenic lines when compared with the infected control lines.

Our preliminary results suggest that silencing these important parasitism genes of CLEs through plant-derived RNAi may generate enhanced or broad resistance to potato cyst nematodes. Potato plants/cultivars with novel resistance to potato cyst nematode pests are much needed in potato cyst nematode eradication and management programs.

Computer Analyses:

BLASTP searches against the GenBank databases at the NCBI website (retrieved from the Internet: <URL: (www.ncbi.nlm.nih.gov/BLAST/; Altschul et al., supra) were performed to identify CLE protein homologues. Signal peptide analysis and protein sequence alignment were conducted using the SignalP program (Nielsen et al. 1997. *Protein Engng.* 10:1-6) and the CLUSTALX program (Thompson et al. 1997. *Nucleic Acids Res.* 25:4876-4882), respectively.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated polynucleotide that produces a double stranded ribonucleotide hairpin, said polynucleotide consisting of a fragment of at least 21 contiguous nucleotides of a nucleic acid which encodes SEQ ID NO:23, and a reverse complement of said fragment; wherein uptake by a *Globodera rostochiensis* nematode of the double stranded ribonucleotide hairpin inhibits the growth of said nematode.

2. An isolated double stranded ribonucleotide molecule produced from the expression of the polynucleotide according to claim 1, wherein the taking up of said double stranded ribonucleotide molecule by a *G. rostochiensis* parasitic nematode inhibits the growth of said nematode.

3. An isolated double stranded ribonucleotide molecule, defined as produced by preparing a recombinant polynucleotide molecule comprising a first and a second polynucleotide sequence, wherein the first polynucleotide sequence consists of an isolated polynucleotide molecule which encodes SEQ ID NO:23, wherein the second polynucleotide sequence is substantially the reverse complement of the first polynucleotide sequence such that the first and the second polynucleotide sequences hybridize when the recombinant polynucleotide molecule is transcribed into a ribonucleic acid molecule that forms the double stranded ribonucleotide molecule, wherein the double stranded ribonucleotide molecule inhibits the growth of a *G. rostochiensis* nematode.

4. A plant transformation vector comprising a polynucleotide molecule that produces a double stranded ribonucleotide molecule, said polynucleotide molecule consisting of a fragment of at least 21 contiguous nucleotides of a nucleic acid which encodes SEQ ID NO:23, and a reverse complement of said fragment; wherein uptake by a *G. rostochiensis* nematode of the double stranded ribonucleotide molecule inhibits the growth of said nematode, and wherein the polynucleotide molecule is operably linked to a heterologous promoter functional in a plant cell.

5. A transgenic plant transformed with the polynucleotide of claim 1 operably linked to a heterologous promoter functional in a plant cell.

6. The transgenic plant of claim 5, wherein the polynucleotide is expressed in an amount effective to reduce, inhibit, or prevent nematode disease caused by *G. rostochiensis* compared to a control plant.

7. A method for controlling a *G. rostochiensis* parasitic nematode population, comprising: providing to a *G. rostochiensis* nematode an agent comprising a double stranded ribonucleotide molecule that functions upon being taken up by the nematode to inhibit a biological function within said nematode, wherein the double stranded ribonucleotide molecule is transcribed from an isolated polynucleotide consisting of a fragment of at least 21 contiguous nucleotides of a nucleic acid which encodes SEQ ID NO:23, and a reverse complement of said fragment; wherein uptake by a *G. rostochiensis* nematode of the double stranded ribonucleotide molecule inhibits the growth of said nematode.

* * * * *

SEQUENCE LISTING

```
<160> NUMBER OF SEQ ID NOS: 27

<210> SEQ ID NO 1
<211> LENGTH: 910
<212> TYPE: DNA
<213> ORGANISM: Globodera rostochiensis

<400> SEQUENCE: 1

tattaatatt gactaatttt tttttacaaa catattaata ttgactaaaa aaattgattt     60

taataacgac tatagatatt acttatggag caacaaaaat cgtcatattt cccatcaaat    120

tcaaataaaa caatctctcc aataaagtaa atatggccaa gaacgcaatg ctttgcctgc    180

tgattttgag cgttgttctt gctctcgcat ttgctacaaa tgaaaaggat gataaagaag    240

cggggaacct ttcgaccggc atttttggaa aggccggaag atttgtgacc gtggcacttg    300

cgatgtcgtc tcgtctggga ggggctggcg catcccaagg aggtggagct gtacatggag    360

aaagcttgaa atccaatcaa ttgcaaaacg cctatcggat ggcgcttcct cctccaatgc    420

aaataaaaag tgccgaaatt gacggatgga aaccgtctcc tgatgaatat cttaaaaaat    480

ttgctcaaga atttcgccga aacaccggta tgaaacccca gtcgtataat gaagagaagc    540

gtgtaacgcc gggagggccc gacccactac ataaccgtga aaaaattctg gaagaacaga    600

agcgtgtaac gccgggaggg cctgacccac tacataaccg tgaaaaaact ctggaagaac    660

agaagcgtgt aacgccggga gggcctgacc cactacataa ccgtgaaaaa actctggaag    720

aacagaagcg tgtaacgccg ggagtgcccg accgacaaca tcgctgaggc aatacaaaaa    780

gagtgaaaga aaatcgacgg atgtctttag taatttcaat tcgttcctat ctttctcgtt    840

ctgaagacca aatatcgatg atgttaatgt tatgttcgga aaacaatttc tgatatgcgc    900

acacttggca                                                           910
```

-continued

<210> SEQ ID NO 2
<211> LENGTH: 1096
<212> TYPE: DNA
<213> ORGANISM: Globodera rostochiensis

<400> SEQUENCE: 2
tattaatatt gactaatttt tttttacaaa catattaata ttgactaaaa aaattgattt 60
taataacgac tatagatatt acttatggag caacaaaaat cgtcatattt cccatcaaat 120
tcaaataaaa caatctctcc aataaagtaa atatggccaa gaacgcaatg ctttgcctgc 180
tgattttgag cgttgttctt gctctcgcat ttgctacaaa tgaaaagggt cagtttccca 240
acaaaaacgt ttatgacccc cctctgacac ctacaaaaaa tcttattttt tttctgaaat 300
tttaattata aaagcctaaa atttgaattt ggtatattta aaatttaaca taaatttggc 360
ataaagatga taaagaagcg gggaaccttt cgaccggcat ttttggaaag gccggaagat 420
ttgtgaccgt ggcacttgcg atgtcgtctc gtctgggagg ggctggcgca tcccaaggag 480
gtggagctgt acatggagaa agcttgaaat ccaatcaatt gcaaaacgcc tatcggatgg 540
tatacaacct actggttgac caaacaaaaa acaattgcaa ttttacaggc gcttcctcct 600
ccaatgcaaa taaaaagtgc cgaaattgac ggatggaaac cgtctcctga tgaatatctt 660
aaaaaatttg ctcaagaatt tcgccgaaac accggtatga aaccccagtc gtataatgaa 720
gagaagcgtg taacgccggg agggcccgac ccactacata accgtgaaaa aattctggaa 780
gaacagaagc gtgtaacgcc gggagggcct gacccactac ataaccgtga aaaaactctg 840
gaagaacaga agcgtgtaac gccgggaggg cctgacccac tacataaccg tgaaaaaact 900
ctggaagaac agaagcgtgt aacgccggga gtgcccgacc gacaacatcg ctgaggcaat 960
acaaaaagag tgaaagaaaa tcgacggatg tctttagtaa tttcaattcg ttcctatctt 1020
tctcgttctg aagaccaaat atcgatgatg ttaatgttat gttcggaaaa caatttctga 1080
tatgcgcaca cttggc 1096

<210> SEQ ID NO 3
<211> LENGTH: 753
<212> TYPE: DNA
<213> ORGANISM: Globodera rostochiensis

<400> SEQUENCE: 3
atcataattt ccaaaatccc aataaaagct tcctcaataa agtaaatatg gccaagaacg 60
caatgctttg cctgttaatt ttgagggttg ttctcgctct cgcatttgct acgaataaaa 120
agggtgatga agaaccggag aaccattcga ccggcatttt tggaaaggtc ggacgagttg 180
tgaccgtggc acttgcgatg tcgtctcgtc tgggaggggc tgacgcaacc cgaggaggtg 240
gagctgtata tggaggaaac ttgaaatcca atcaattgcc aaacaacaat tggatggcgc 300
cacctcctcc aatggcaatt agaagtgcca aagtctatga ttcgaaacat tctcctgctg 360
aatatcttaa aaaatttgct caagactttc gccgaaaaac cggcatgcac tcccagcggc 420
atcacgaaga aacaacactg gaacaggaga agcgtgtagc gggagctggt cccgacccaa 480
tacatcacca agatacaaca ctggaacagg agaagcgtgc agtcccagct gggcccgacc 540
caaaacatca cgaagaaaca acactggaac aggagaagcg tgcagtccca gctgggcccg 600
acccaaaaca tcacgaagat acaacactgg aacaggagaa gcgtggtgcg ccagctgggc 660
ccgacccaat acatcactga tgctcttatt cacaatgcta aaatatctgt agactataga 720
taaattgcta gcaacagata aatgcctgat cat 753

-continued

<210> SEQ ID NO 4
<211> LENGTH: 1000
<212> TYPE: DNA
<213> ORGANISM: Globodera rostochiensis

<400> SEQUENCE: 4
atcataattt ccaaaatccc aataaaagct tcctcaataa agtaaatatg gccacgaaca 60
caatgctttg cctgttaatt ttgagcgttg ttctcgctct cgcatttgct acgaataaaa 120
agggtgatga agaaccggag aaccattcga ccggcatttt tggaaaggtc ggacgagttg 180
tgaccgtggc acttgcgatg tcgtctcgtc tgggaggggc tgacgcaacc cgaggaggtg 240
gagctgtata tggaggaaac ttgaaatcca atctattgcc aaacaacaat tggatggcgc 300
cacctcctcc aatggcaatg agaagtgcca aagtctatga ttcgaaacat tctcctgctg 360
aatatcttaa aaaatttgct caagactttc gccgaaaaac cggcatgcac tcccagcggc 420
atcacgaaga aacaacactg gaacaggaga agcgtgtagc gggagctggt cccgacccaa 480
tacatcacca agatacaaca ctggaacagg agaagcgtgc agtcccagct gggcccgacc 540
caaaacatca cgaagaaaca acactggaac aggagaagcg tgcagtccca gctgggcccg 600
acccaaaaca tcacgaagaa acaacactgg aacaggagaa gcgtgcagtc ccagctgggc 660
ccgacccaaa acatcacgaa gaaacaacat ttgaacagga gaagcgtggt gcgccagctg 720
ggcccgaccc aatacatcac tgatgctctt attcacaatg ctaaaatatc tgtagactat 780
agataaattg ctagcaacag ataaatgcct gatcataatg ctatggctaa ggtatccgta 840
ttccgaacta gcaatataag cgcatgcgta gctctatcca tttaatttca caatctaaag 900
attaaaatct gcagatatct agctgtagct gggctatctg cggatggaaa aatcggcatt 960
cttaatataa tttttaattg cttaataaac ttcaataaaa 1000

<210> SEQ ID NO 5
<211> LENGTH: 548
<212> TYPE: DNA
<213> ORGANISM: Globodera rostochiensis

<400> SEQUENCE: 5
atcataattt ccaaaatccc aataaaagct tcctcaataa agtaaatatg gccacgaaca 60
caatgctttg cctgtttgtt ataagcgttg ttctcgctct cgcatttgct acgaataaaa 120
agggtgatga agaaccggag aaccattcga ccggcatttt tggaaaggtc ggacgagttg 180
tgaccgtggc acttgcgatg tcgtctcgtc tgggaggggc tgacgcaacc cgaggaggtg 240
gagctgtata tggaggaaac ttgaaatcca atcaattgcc aaacaacaat tggatggcgc 300
cacctcctcc aatggcaata agaagtgcca aagtctatga ttcgaaacat tctcctgctg 360
aatatcttaa aaaatttgct caagactttc gccgaaaaac cggcatgcac tcccagcggc 420
atcacgaaga aacaacactg gaacaggaga agcgtgtagc gggagctggt cccgacccaa 480
tacatcactg atgctcttat tcacaatgct aaaatatctg tagactatag ataaattgct 540
agcaacag 548

<210> SEQ ID NO 6
<211> LENGTH: 752
<212> TYPE: DNA
<213> ORGANISM: Globodera rostochiensis

<400> SEQUENCE: 6
atcataattt ccaaaatccc aataaaagct tcctcaataa agtaaatatg gccaagaacg 60

```
caatgctttg cctgctaatt ttgagcgttg ttctcgctct cgcatttgct acgaataaaa    120

aggatgatga agaaccggag aaccattcga ccggcatttt tggaaaggtc ggacgagttg    180

tgaccgtggc acttgcgatg tcgtctcgtc tgggaggggc taacgcaacc cgaggaggtg    240

gagctgtata tggaagaaac ttgaaatcca atcaattgcc aaacaacaat tggatggcgc    300

cacctcctcc aatggcaatg agaagtgcca aagtctatga ttcgaaacat tctcctgctg    360

aatatcttaa aaaatttgct caagactttc gccgaaaaac cggcacgcac tcccagcggc    420

atcacgaaga aacaacactg gaacaggaga agcgtggagc gccagctggg cccgacccaa    480

tacatcacca agatacaaca tttgaacagg agaagcgtgg agcgccagct gggcccgacc    540

caatacatca ccaagataca acactggaac aggagaagcg tgtagcggga gctgggcccg    600

acccaataca tcaccaagat acaaaatttg aacaggagaa gcgtggagcg ccagctgggc    660

ccgacccaat acatcactga tgctcttatt cacaatgcta aaatatttta gactatagat    720

aaattgctag caacagataa atgcctattc at                                  752
```

<210> SEQ ID NO 7
<211> LENGTH: 1038
<212> TYPE: DNA
<213> ORGANISM: Globodera rostochiensis

<400> SEQUENCE: 7

```
atcataattt ccaaaatccc aataaaagct tcctcaataa agtaaatatg gccaagaacg     60

caatgctttg cctgttaatt ttgagggttg ttctcgctct cgcatttgct acgaataaaa    120

agggtcagtt cccgagacaa aaacgtttat gaccccctac tgacactaaa atttaaaatt    180

ttattacaaa gacctaaatt gtaatttgct atattattat acttaacctt aaattgaaat    240

aaaggtgatg aagaaccgga gaaccattcg accggcattt ttggaaaggt cggacgagtt    300

gtgaccgtgg cacttgcgat gtcgtctcgt ctgggagggg ctgacgcaac ccgaggaggt    360

ggagctgtat atggaggaaa cttgaaatcc aatcaattgc caaacaacaa ttggatggta    420

tccaccgaca ggttgaacaa ggaataaaca ttttacaatt ttacaggcgc cacctcctcc    480

aatggcaatt agaagtgcca aagtctatga ttcgaaacat tctcctgctg aatatcttaa    540

aaaatttgct caagactttc gccgaaaaac cggcatgcac tcccagcggc atcacgaaga    600

aacaacactg gaacaggaga agcgtgtagc gggagctggt cccgacccaa tacatcacca    660

agatacaaca ctggaacagg agaagcgtgc agtcccagct gggcccgacc caaaacatca    720

cgaagaaaca acactggaac aggagaagcg tgcagtccca gctgggcccg acccaaaaca    780

tcacgaagat acaacactgg aacaggagaa gcgtggtgcg ccagctgggc ccgacccaat    840

acatcactga tgctcttatt cacaatgcta aaatatctgt agactataga taaattgcta    900

gcaacagata aatgcctgat cataatgcta tggctaaggt atccgtattc cgaactagca    960

atataagcgc atgcgtagct ctatccattt aatttcacaa tctaaagatt aaaatctgca   1020

gatatctagc tgtagctg                                                 1038
```

<210> SEQ ID NO 8
<211> LENGTH: 1085
<212> TYPE: DNA
<213> ORGANISM: Globodera rostochiensis

<400> SEQUENCE: 8

```
tcccaataaa agcttcctca ataaagtaaa tatggccacg aacacaatgc tttgcctgtt     60

aattttgagc gttgttctcg ctctcgcatt tgctacgaat aaaaagggtc agttcccgag    120
```

acaaaaacgt ttatgacccc ctactgacac taaaatttaa aattttatta caaagaccta 180
aattttaatt tgctatatta ttatacttaa ccttaaattg aaataaaggt gatgaagaac 240
cggagaacca ttcgaccggc atttttggaa aggtcggacg agttgtgacc gtggcacttg 300
cgatgtcgtc tcgtctggga ggggctgacg caacccgagg aggtggagct gtatatggag 360
gaaacttgaa atccaatcta ttgccaaaca acaattggat ggtatccacc gacaggttga 420
acaaggaata aacattttac aattttacag gcgccacctc ctccaatggc aatgagaagt 480
gccaaagtct atgattcgaa acattctcct gctgaatatc ttaaaaaatt tgctcaagac 540
tttcgccgaa aaaccggcat gcactcccag cggcatcacg aagaaacaac actggaacag 600
gagaagcgtg tagcgggagc tggtcccgac ccaatacatc accaagatac aacactggaa 660
caggagaagc gtgcagtccc agctgggccc gacccaaaac atcacgaaga aacaacactg 720
gaacaggaga agcgtgcagt cccagctggg cccgacccaa aacatcacga agaaacaaca 780
ctggaacagg agaagcgtgc agtcccagct gggcccgacc caaaacatca cgaagaaaca 840
acatttgaac aggagaagcg tggtgcgcca gctgggcccg acccaataca tcactgatgc 900
tcttattcac aatgctaaaa tatctgtaga ctatagataa attgctagca acagataaat 960
gcctgatcat aatgctatgg ctaaggtatc cgtattccga actagcaata taagcgcatg 1020
cgtagctcta tccatttaat ttcacaatct aaagattaaa atctgcagat atctagctgt 1080
agctg 1085

<210> SEQ ID NO 9
<211> LENGTH: 915
<212> TYPE: DNA
<213> ORGANISM: Globodera rostochiensis

<400> SEQUENCE: 9
atcataattt ccaaaatccc aataaaagct tcctcaataa agtaaatatg gccacgaaca 60
caatgctttg cctgtttgtt ataagcgttg ttctcgctct cgcatttgct acgaataaaa 120
agggtcagtt cccgagacaa aaacgtttat ggccaactac taacacaaaa atttaaaatt 180
tcattacaag gacctaaatt gtaatttgct atattattat acttaacctt aaattgaaat 240
aaaggtgatg aagaaccgga gaaccattcg accggcattt ttggaaaggt cggacgagtt 300
gtgaccgtgg cacttgcgat gtcgtctcgt ctgggagggg ctgacgcaac ccgaggaggt 360
ggagctgtat atggaggaaa cttgaaatcc aatcaattgc caaacaacaa ttggatggta 420
tccaccgaca ggttgaacaa ggaataaaca ttttactatt ttacaggcgc cacctcctcc 480
aatggcaata agaagtgcca aagtctatga ttcgaaacat tctcctgctg aatatcttaa 540
aaaatttgct caagactttc gccgaaaaac cggcatgcac tcccagcggc atcacgaaga 600
aacaacactg gaacaggaga agcgtgtagc gggagctggt cccgacccaa tacatcactg 660
atgctcttat tcacaatgct aaaatatctg tagactatag ataaattgct agcaacagat 720
aaatgcctga tcataatgct atggctaagg tatccgtatt ccgaactagc aatataatcg 780
ctatgcgtag ctctatccat ttaatttcac aatctaaaga ttaaaatctg cagatatcta 840
gctgtagctg ggctatctgc ggatggaaaa atcggcattc ttaatataat ttttaattgc 900
ttaataaact tcaat 915

<210> SEQ ID NO 10
<211> LENGTH: 1103
<212> TYPE: DNA
<213> ORGANISM: Globodera rostochiensis -continued

<400> SEQUENCE: 10
atcataattt ccaaaatccc aataaaagct tcctcaataa agtaaatatg gccaagaacg 60
caatgctttg cctgctaatt ttgagcgttg ttctcgctct cgcatttgct acgaataaaa 120
agggtcagtt cccgagacaa aaacgtttat ggccccctac taacactaaa atttaaaatt 180
tcattacaaa gacctaaatt gtaatttgct atattattat acttaacctt aaattggcat 240
aaagatgatg aagaaccgga gaaccattcg accggcattt ttggaaaggt cggacgagtt 300
gtgaccgtgg cacttgcgat gtcgtctcgt ctgggagggg ctaacgcaac ccgaggaggt 360
ggagctgtat atggaagaaa cttgaaatcc aatcaattgc caaacaacaa ttggatggta 420
acctaccgac aggtttaaca aggaataaac attttacaat tttacaggcg ccacctcctc 480
caatggcaat gagaagtgcc aaagtctatg attcgaaaca ttctcctgct gaatatctta 540
aaaaatttgc tcaagacttt cgccgaaaaa ccggcacgca ctcccagcgg catcacgaag 600
aaacaacact ggaacaggag aagcgtggag cgccagctgg gcccgaccca atacatcacc 660
aagatacaac atttgaacag gagaagcgtg gagcgccagc tgggcccgac ccaatacatc 720
accaagatac aacactggaa caggagaagc gtgtagcggg agctgggccc gacccaatac 780
atcaccaaga tacaaaattt gaacaggaga agcgtggagc gccagctggg cccgacccaa 840
tacatcactg atgctcttat tcacaatgct aaaatatttt agactataga taaattgcta 900
gcaacagata aatgcctatt cataatgcta tggctaaggt atccgtattc cgaactagca 960
atataatcgc tatgcgtagc tctatccatt taatttcaca atctaaagat taaaatctgc 1020
agatatctag ctgtagctgg gctatctgcg gatggaaaaa gcggattctt aatataattt 1080
ttaattgctt aataaacttc aat 1103

<210> SEQ ID NO 11
<211> LENGTH: 567
<212> TYPE: DNA
<213> ORGANISM: Globodera rostochiensis

<400> SEQUENCE: 11
atggccaaga acgcaatgct atacctggtg attttgagcg ttattctcgc tcttgcattt 60
gctacaaatg aaagggatga taaagaagcg gagaaccatt cggccggcat tttggaaag 120 gtcggacgat ctgtgaccgt gacacttgcg atgtcgtctc gtctgggagg ggctggcgca 180
tcccgagaag ttggagctgt acatggagta aacttgaaat acaatcaatt gccaaacaac 240
aattggatgg cgcctcctcc tcctccaatg cctatgaaaa gtgccgaatt caatgtcaga 300
aagccttctc ctgctgaatc tcttaaaaaa tttgctcatg aatttcgcca aaacaccggc 360
atgaaacctc agtggtataa tgaagagaag cgtgtatcgc cgggagggcc cgaccctcac 420
cataacggag aagtgaaccg tctatcgccg ggagggcccg accctcacca taacggagaa 480
gtggaccgtc tatcgccggg agggcccgac cctcaccata acgggcaagt aaaccgtcta 540
acagtgcccg accgacaaca tcgctga 567

<210> SEQ ID NO 12
<211> LENGTH: 12
<212> TYPE: PRT
<213> ORGANISM: Globodera rostochiensis

<400> SEQUENCE: 12

Arg Val Ile Pro Gly Gly Pro Asp Pro Leu His Asn
1 5 10

<210> SEQ ID NO 13
<211> LENGTH: 12
<212> TYPE: PRT
<213> ORGANISM: Globodera rostochiensis

<400> SEQUENCE: 13

Arg Val Ile Pro Gly Ala Pro Asp Pro Leu His Asn
1 5 10

<210> SEQ ID NO 14
<211> LENGTH: 14
<212> TYPE: PRT
<213> ORGANISM: Globodera rostochiensis

<400> SEQUENCE: 14

Lys Arg Val Ile Pro Gly Gly Pro Asp Pro Leu His Asn Arg
1 5 10

<210> SEQ ID NO 15
<211> LENGTH: 12
<212> TYPE: PRT
<213> ORGANISM: Globodera rostochiensis

<400> SEQUENCE: 15

Arg Val Ala Gly Ala Gly Pro Asp Pro Ile His His
1 5 10

<210> SEQ ID NO 16
<211> LENGTH: 13
<212> TYPE: PRT
<213> ORGANISM: Globodera rostochiensis

<400> SEQUENCE: 16

Leu Arg Val Ala Gly Ala Gly Pro Asp Pro Ile His His
1 5 10

<210> SEQ ID NO 17
<211> LENGTH: 12
<212> TYPE: PRT
<213> ORGANISM: Globodera rostochiensis

<400> SEQUENCE: 17

Arg Ala Val Pro Ala Gly Pro Asp Pro Leu His His
1 5 10

<210> SEQ ID NO 18
<211> LENGTH: 13
<212> TYPE: PRT
<213> ORGANISM: Globodera rostochiensis

<400> SEQUENCE: 18

Leu Arg Ala Val Pro Ala Gly Pro Asp Pro Leu His His
1 5 10

<210> SEQ ID NO 19
<211> LENGTH: 12
<212> TYPE: PRT
<213> ORGANISM: Globodera rostochiensis

<400> SEQUENCE: 19

Arg Gly Ala Pro Ala Gly Pro Asp Pro Ile His His
1 5 10

<210> SEQ ID NO 20
<211> LENGTH: 13

<212> TYPE: PRT
<213> ORGANISM: Globodera rostochiensis

<400> SEQUENCE: 20

```
Leu Arg Gly Ala Pro Ala Gly Pro Asp Pro Ile His His
1               5                   10
```

<210> SEQ ID NO 21
<211> LENGTH: 12
<212> TYPE: PRT
<213> ORGANISM: Globodera rostochiensis

<400> SEQUENCE: 21

```
Arg Thr Val Pro Ser Gly Pro Asp Pro Leu His His
1               5                   10
```

<210> SEQ ID NO 22
<211> LENGTH: 16
<212> TYPE: PRT
<213> ORGANISM: Globodera rostochiensis

<400> SEQUENCE: 22

```
Ala Pro Asn Asn His His Tyr Ser Ser Ala Gly Arg Gln Asp Gln Thr
1               5                   10                  15
```

<210> SEQ ID NO 23
<211> LENGTH: 204
<212> TYPE: PRT
<213> ORGANISM: Globodera rostochiensis

<400> SEQUENCE: 23

```
Met Ala Lys Asn Ala Met Leu Cys Leu Leu Ile Leu Ser Val Val Leu
1               5                   10                  15

Ala Leu Ala Phe Ala Thr Asn Glu Lys Asp Asp Lys Glu Ala Gly Asn
            20                  25                  30

Leu Ser Thr Gly Ile Phe Gly Lys Ala Gly Arg Phe Val Thr Val Ala
        35                  40                  45

Leu Ala Met Ser Ser Arg Leu Gly Gly Ala Gly Ala Ser Gln Gly Gly
    50                  55                  60

Gly Ala Val His Gly Glu Ser Leu Lys Ser Asn Gln Leu Gln Asn Ala
65                  70                  75                  80

Tyr Arg Met Ala Leu Pro Pro Pro Met Gln Ile Lys Ser Ala Glu Ile
                85                  90                  95

Asp Gly Trp Lys Pro Ser Pro Asp Glu Tyr Leu Lys Lys Phe Ala Gln
            100                 105                 110

Glu Phe Arg Arg Asn Thr Gly Met Lys Pro Gln Ser Tyr Asn Glu Glu
        115                 120                 125

Lys Arg Val Thr Pro Gly Gly Pro Asp Pro Leu His Asn Arg Glu Lys
    130                 135                 140

Ile Leu Glu Glu Gln Lys Arg Val Thr Pro Gly Gly Pro Asp Pro Leu
145                 150                 155                 160

His Asn Arg Glu Lys Thr Leu Glu Glu Gln Lys Arg Val Thr Pro Gly
                165                 170                 175

Gly Pro Asp Pro Leu His Asn Arg Glu Lys Thr Leu Glu Glu Gln Lys
            180                 185                 190

Arg Val Thr Pro Gly Val Pro Asp Arg Gln His Arg
        195                 200
```

<210> SEQ ID NO 24
<211> LENGTH: 210

-continued

<212> TYPE: PRT
<213> ORGANISM: Globodera rostochiensis

<400> SEQUENCE: 24

```
Met Ala Lys Asn Ala Met Leu Cys Leu Leu Ile Leu Arg Val Val Leu
1               5                   10                  15

Ala Leu Ala Phe Ala Thr Asn Lys Lys Gly Asp Glu Glu Pro Glu Asn
            20                  25                  30

His Ser Thr Gly Ile Phe Gly Lys Val Gly Arg Val Val Thr Val Ala
        35                  40                  45

Leu Ala Met Ser Ser Arg Leu Gly Gly Ala Asp Ala Thr Arg Gly Gly
    50                  55                  60

Gly Ala Val Tyr Gly Gly Asn Leu Lys Ser Asn Gln Leu Pro Asn Asn
65                  70                  75                  80

Asn Trp Met Ala Pro Pro Pro Pro Met Ala Ile Arg Ser Ala Lys Val
                85                  90                  95

Tyr Asp Ser Lys His Ser Pro Ala Glu Tyr Leu Lys Lys Phe Ala Gln
            100                 105                 110

Asp Phe Arg Arg Lys Thr Gly Met His Ser Gln Arg His His Glu Glu
        115                 120                 125

Thr Thr Leu Glu Gln Glu Lys Arg Val Ala Gly Ala Gly Pro Asp Pro
    130                 135                 140

Ile His His Gln Asp Thr Thr Leu Glu Gln Glu Lys Arg Ala Val Pro
145                 150                 155                 160

Ala Gly Pro Asp Pro Lys His His Glu Glu Thr Thr Leu Glu Gln Glu
                165                 170                 175

Lys Arg Ala Val Pro Ala Gly Pro Asp Pro Lys His His Glu Asp Thr
            180                 185                 190

Thr Leu Glu Gln Glu Lys Arg Gly Ala Pro Ala Gly Pro Asp Pro Ile
        195                 200                 205

His His
    210
```

<210> SEQ ID NO 25
<211> LENGTH: 231
<212> TYPE: PRT
<213> ORGANISM: Globodera rostochiensis

<400> SEQUENCE: 25

```
Met Ala Thr Asn Thr Met Leu Cys Leu Leu Ile Leu Ser Val Val Leu
1               5                   10                  15

Ala Leu Ala Phe Ala Thr Asn Lys Lys Gly Asp Glu Glu Pro Glu Asn
            20                  25                  30

His Ser Thr Gly Ile Phe Gly Lys Val Gly Arg Val Val Thr Val Ala
        35                  40                  45

Leu Ala Met Ser Ser Arg Leu Gly Gly Ala Asp Ala Thr Arg Gly Gly
    50                  55                  60

Gly Ala Val Tyr Gly Gly Asn Leu Lys Ser Asn Leu Leu Pro Asn Asn
65                  70                  75                  80

Asn Trp Met Ala Pro Pro Pro Pro Met Ala Met Arg Ser Ala Lys Val
                85                  90                  95

Tyr Asp Ser Lys His Ser Pro Ala Glu Tyr Leu Lys Lys Phe Ala Gln
            100                 105                 110

Asp Phe Arg Arg Lys Thr Gly Met His Ser Gln Arg His His Glu Glu
        115                 120                 125

Thr Thr Leu Glu Gln Glu Lys Arg Val Ala Gly Ala Gly Pro Asp Pro
```

-continued

```
    130                 135                 140

Ile His His Gln Asp Thr Thr Leu Glu Gln Glu Lys Arg Ala Val Pro
145                 150                 155                 160

Ala Gly Pro Asp Pro Lys His His Glu Glu Thr Thr Leu Glu Gln Glu
                165                 170                 175

Lys Arg Ala Val Pro Ala Gly Pro Asp Pro Lys His His Glu Glu Thr
            180                 185                 190

Thr Leu Glu Gln Glu Lys Arg Ala Val Pro Ala Gly Pro Asp Pro Lys
        195                 200                 205

His His Glu Glu Thr Thr Phe Glu Gln Glu Lys Arg Gly Ala Pro Ala
    210                 215                 220

Gly Pro Asp Pro Ile His His
225                 230


<210> SEQ ID NO 26
<211> LENGTH: 147
<212> TYPE: PRT
<213> ORGANISM: Globodera rostochiensis

<400> SEQUENCE: 26

Met Ala Thr Asn Thr Met Leu Cys Leu Phe Val Ile Ser Val Val Leu
1               5                   10                  15

Ala Leu Ala Phe Ala Thr Asn Lys Lys Gly Asp Glu Glu Pro Glu Asn
            20                  25                  30

His Ser Thr Gly Ile Phe Gly Lys Val Gly Arg Val Val Thr Val Ala
        35                  40                  45

Leu Ala Met Ser Ser Arg Leu Gly Gly Ala Asp Ala Thr Arg Gly Gly
    50                  55                  60

Gly Ala Val Tyr Gly Gly Asn Leu Lys Ser Asn Gln Leu Pro Asn Asn
65                  70                  75                  80

Asn Trp Met Ala Pro Pro Pro Pro Met Ala Ile Arg Ser Ala Lys Val
                85                  90                  95

Tyr Asp Ser Lys His Ser Pro Ala Glu Tyr Leu Lys Lys Phe Ala Gln
            100                 105                 110

Asp Phe Arg Arg Lys Thr Gly Met His Ser Gln Arg His His Glu Glu
        115                 120                 125

Thr Thr Leu Glu Gln Glu Lys Arg Val Ala Gly Ala Gly Pro Asp Pro
    130                 135                 140

Ile His His
145


<210> SEQ ID NO 27
<211> LENGTH: 210
<212> TYPE: PRT
<213> ORGANISM: Globodera rostochiensis

<400> SEQUENCE: 27

Met Ala Lys Asn Ala Met Leu Cys Leu Leu Ile Leu Ser Val Val Leu
1               5                   10                  15

Ala Leu Ala Phe Ala Thr Asn Lys Lys Asp Asp Glu Glu Pro Glu Asn
            20                  25                  30

His Ser Thr Gly Ile Phe Gly Lys Val Gly Arg Val Val Thr Val Ala
        35                  40                  45

Leu Ala Met Ser Ser Arg Leu Gly Gly Ala Asn Ala Thr Arg Gly Gly
    50                  55                  60

Gly Ala Val Tyr Gly Arg Asn Leu Lys Ser Asn Gln Leu Pro Asn Asn
65                  70                  75                  80
```

-continued

```
Asn Trp Met Ala Pro Pro Pro Pro Met Ala Met Arg Ser Ala Lys Val
                85                  90                  95

Tyr Asp Ser Lys His Ser Pro Ala Glu Tyr Leu Lys Lys Phe Ala Gln
            100                 105                 110

Asp Phe Arg Arg Lys Thr Gly Thr His Ser Gln Arg His His Glu Glu
        115                 120                 125

Thr Thr Leu Glu Gln Glu Lys Arg Gly Ala Pro Ala Gly Pro Asp Pro
    130                 135                 140

Ile His His Gln Asp Thr Thr Phe Glu Gln Glu Lys Arg Gly Ala Pro
145                 150                 155                 160

Ala Gly Pro Asp Pro Ile His His Gln Asp Thr Thr Leu Glu Gln Glu
                165                 170                 175

Lys Arg Val Ala Gly Ala Gly Pro Asp Pro Ile His His Gln Asp Thr
            180                 185                 190

Lys Phe Glu Gln Glu Lys Arg Gly Ala Pro Ala Gly Pro Asp Pro Ile
        195                 200                 205

His His
    210
```